(12) United States Patent
Machold et al.

(10) Patent No.: US 9,861,475 B2
(45) Date of Patent: Jan. 9, 2018

(54) DEVICES, SYSTEMS, AND METHODS FOR RESHAPING A HEART VALVE ANNULUS

(75) Inventors: Timothy R. Machold, Moss Beach, CA (US); David A. Rahdert, San Francisco, CA (US); John A. Macoviak, La Jolla, CA (US); Robert T. Chang, Belmont, CA (US); Rick A. Soss, Burlingame, CA (US)

(73) Assignee: MVRX INC., San Mateo, CA (US)

(\*) Notice: Subject to any disclaimer, the term of this patent is extended or adjusted under 35 U.S.C. 154(b) by 1218 days.

(21) Appl. No.: 12/462,956

(22) Filed: Aug. 12, 2009

(65) Prior Publication Data
US 2009/0306622 A1    Dec. 10, 2009

Related U.S. Application Data

(63) Continuation of application No. 10/677,104, filed on Oct. 1, 2003, now abandoned.

(60) Provisional application No. 60/429,444, filed on Nov. 26, 2002.

(51) Int. Cl.
*A61F 2/24* (2006.01)
*A61B 17/00* (2006.01)

(52) U.S. Cl.
CPC .......... *A61F 2/2418* (2013.01); *A61F 2/2445* (2013.01); *A61F 2/2454* (2013.01); *A61F 2/2466* (2013.01); *A61B 2017/00243* (2013.01); *A61F 2220/0016* (2013.01)

(58) Field of Classification Search
CPC .... A61F 2/2487; A61F 2/2442; A61F 2/2445; A61F 2/2448

USPC ................ 600/37; 623/2.36, 2.37, 2.38, 2.1; 606/151, 157, 158
See application file for complete search history.

(56) References Cited

U.S. PATENT DOCUMENTS

| | | | |
|---|---|---|---|
| 4,056,854 A | 11/1977 | Boretos et al. | |
| 4,275,469 A | 6/1981 | Gabbay | |
| 4,491,986 A * | 1/1985 | Gabbay | ........................ 623/2.18 |
| 4,994,069 A | 2/1991 | Ritchart et al. | |
| 5,360,444 A | 11/1994 | Kusuhara | |
| 5,370,685 A | 12/1994 | Stevens | |

(Continued)

OTHER PUBLICATIONS de Silva et al. "Postinfarction Ventricular Septal Defect. An Efficacious Technique for Early Surgical Repair." J Throac Cardiovasc Surg. Jan. 1989; 97(1):86-9.

(Continued)

*Primary Examiner* — Alvin Stewart
(74) *Attorney, Agent, or Firm* — Kilpatrick, Townsend & Stockton LLP

(57) ABSTRACT

Devices, systems, and methods employ an implant that is sized and configured to attach to the annulus of a dysfunctional heart valve annulus. In use, the implant extends across the major axis of the annulus above and/or along the valve annulus. The implant reshapes the major axis dimension and/or other surrounding anatomic structures. The implant restores to the heart valve annulus and leaflets a more functional anatomic shape and tension. The more functional anatomic shape and tension are conducive to coaptation of the leaflets during systole, which, in turn, reduces regurgitation. The implant improves function to the valve, without surgically cinching, resecting, and/or fixing in position large portions of a dilated annulus, or without the surgical fixation of ring-like structures.

21 Claims, 30 Drawing Sheets

(56) References Cited

U.S. PATENT DOCUMENTS

| | | | |
|---|---|---|---|
| 5,545,241 A | 8/1996 | Vanderauwera et al. | |
| 5,716,397 A | 2/1998 | Myers | |
| 5,776,189 A | 7/1998 | Khalid | |
| 5,792,155 A | 8/1998 | Van Cleef et al. | |
| 5,830,224 A | 11/1998 | Cohn et al. | |
| 5,855,601 A | 1/1999 | Bessler et al. | |
| 5,961,440 A | 10/1999 | Schweich, Jr. et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,099,542 A | 8/2000 | Cohn et al. | |
| 6,102,932 A | 8/2000 | Kurz | |
| 6,162,168 A | 12/2000 | Schweich, Jr. et al. | |
| 6,165,119 A | 12/2000 | Schweich, Jr. et al. | |
| 6,183,411 B1 | 2/2001 | Mortier et al. | |
| 6,210,432 B1 | 4/2001 | Solem et al. | |
| 6,260,552 B1 | 7/2001 | Mortier et al. | |
| 6,261,222 B1 | 7/2001 | Schweich, Jr. et al. | |
| 6,287,339 B1 | 9/2001 | Vazquez et al. | |
| 6,299,637 B1 | 10/2001 | Shaolian et al. | 623/1.24 |
| 6,312,464 B1 | 11/2001 | Navia | |
| 6,312,465 B1 | 11/2001 | Griffin et al. | |
| 6,332,864 B1 | 12/2001 | Schweich, Jr. et al. | |
| 6,332,893 B1 | 12/2001 | Mortier et al. | |
| 6,338,735 B1 | 1/2002 | Stevens | |
| 6,338,740 B1 | 1/2002 | Carpentier | |
| 6,402,781 B1 | 6/2002 | Langberg et al. | |
| 6,419,695 B1 | 7/2002 | Gabbay | |
| 6,419,696 B1 | 7/2002 | Ortiz et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | 623/1.24 |
| 6,503,272 B2 | 1/2003 | Duerig et al. | 623/1.24 |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,629,534 B1 | 10/2003 | St. Goar et al. | |
| 6,656,221 B2 | 12/2003 | Taylor et al. | |
| 6,669,709 B1 | 12/2003 | Cohn et al. | |
| 6,676,699 B2 | 1/2004 | Shiu | 623/1.24 |
| 6,685,739 B2 | 2/2004 | DiMatteo et al. | 623/1.24 |
| 6,702,826 B2 | 3/2004 | Liddicoat et al. | |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 6,893,459 B1 | 5/2005 | Macoviak | |
| 6,913,608 B2 | 7/2005 | Liddicoat et al. | |
| 6,945,978 B1 | 9/2005 | Hyde | |
| 7,004,176 B2 | 2/2006 | Lau | |
| 7,070,618 B2 | 7/2006 | Streeter | |
| 7,077,862 B2* | 7/2006 | Vidlund et al. | 623/2.36 |
| 7,166,126 B2* | 1/2007 | Spence | A61F 2/2412 |
| | | | 623/2.36 |
| 7,291,168 B2* | 11/2007 | Macoviak | A61F 2/2412 |
| | | | 623/2.36 |
| 7,381,220 B2* | 6/2008 | Macoviak | A61F 2/2445 |
| | | | 623/2.12 |
| 7,452,371 B2* | 11/2008 | Pavcnik et al. | 623/1.24 |
| 7,527,646 B2* | 5/2009 | Randert | A61F 2/2454 |
| | | | 623/2.36 |
| 7,837,727 B2* | 11/2010 | Goetz | A61F 2/2418 |
| | | | 623/1.15 |
| 8,016,882 B2* | 9/2011 | Macoviak | A61F 2/2445 |
| | | | 623/2.36 |
| 8,142,494 B2* | 3/2012 | Randert | A61F 2/2454 |
| | | | 623/2.36 |
| 9,610,161 B2* | 4/2017 | Macoviak | A61F 2/2445 |
| 2001/0010017 A1 | 7/2001 | Letac et al. | |
| 2001/0021872 A1 | 9/2001 | Bailey et al. | |
| 2001/0051824 A1 | 12/2001 | Hopkins et al. | |
| 2002/0032481 A1 | 3/2002 | Gabbay | |
| 2002/0035361 A1* | 3/2002 | Houser et al. | 606/15 |
| 2002/0065554 A1 | 5/2002 | Streeter | |
| 2002/0094573 A1 | 7/2002 | Bell | |
| 2002/0123802 A1 | 9/2002 | Snyders | |
| 2002/0129820 A1 | 9/2002 | Ryan et al. | |
| 2002/0138138 A1 | 9/2002 | Yang | |
| 2003/0014104 A1 | 1/2003 | Cribier | 623/2.11 |
| 2003/0040792 A1 | 2/2003 | Gabbay | |
| 2003/0120340 A1 | 6/2003 | Liska et al. | |
| 2003/0144732 A1* | 7/2003 | Cosgrove et al. | 623/2.11 |
| 2003/0191528 A1* | 10/2003 | Quijano et al. | 623/2.37 |
| 2003/0233022 A1 | 12/2003 | Vidlund et al. | |
| 2004/0127981 A1* | 7/2004 | Randert | A61F 2/2454 |
| | | | 623/2.36 |
| 2004/0127982 A1* | 7/2004 | Machold | A61F 2/2418 |
| | | | 623/2.36 |
| 2004/0148019 A1 | 7/2004 | Vidlund et al. | |
| 2005/0004668 A1* | 1/2005 | Aklog | A61F 2/2454 |
| | | | 623/2.36 |
| 2005/0010287 A1* | 1/2005 | Macoviak | A61F 2/2445 |
| | | | 623/2.36 |
| 2005/0267573 A9* | 12/2005 | Macoviak | A61F 2/2445 |
| | | | 623/2.36 |
| 2006/0052868 A1* | 3/2006 | Mortier | A61F 2/2454 |
| | | | 623/2.36 |
| 2006/0069430 A9* | 3/2006 | Randert | A61F 2/2454 |
| | | | 623/2.36 |
| 2006/0106456 A9* | 5/2006 | Machold | A61F 2/2412 |
| | | | 623/2.36 |
| 2006/0229708 A1* | 10/2006 | Powell | A61B 17/00234 |
| | | | 623/1.24 |
| 2006/0241745 A1 | 10/2006 | Solem | |
| 2008/0140190 A1* | 6/2008 | Macoviak | A61F 2/2412 |
| | | | 623/2.36 |

OTHER PUBLICATIONS

Tashiro et al. "Extended Endocardial Repair of Postinfarction Ventricular Septal Rupture: New Operative Technique-Modification of the Komeda-David-Operation." J Card Surg. Mar. 1994; 9(2):97-102.

Daggett, "Surgical Technique for Early Repair of Posterior Ventricular Septal Rupture." J Thorac Cardiovasc Surg. Aug. 1982;84(2):306-12.

Daggett et al. "Surgery for Post-Myorcardial Infarct Ventricular Septal Defect." Ann Surg. Sep. 1977; 186(3): 260-71.

Dor, "Left Ventricular Aneurysms: the Endoventricular Circular Patch Plasty." Semin Thorac Cardiovasc Surg. Apr. 1997;9(2):123-30.

Antunes, "Submitral Left Ventricular Aneurysms. Correction by a New Transatrial Approach." J Thorac Cardiovasc Surg. Aug. 1987;94(2):241-5.

Alvarez et al. "Technical Improvements in the Repair of Acute Postinfarction Ventricular Septal Rupture." J Card Surg. Sep. 1992;7(3):198-202.

Cox, "Surgical Management of Left Ventricular Aneurysms: A Clarification of the Similarities and Differences Between the Jatene and Dor Techniques." Semin Thorqc Cardiovasc Surg. Apr. 1997;9(2):131-8.

Skillington et al. "Surgical Treatment for Infarct-Related Ventricular Septal Defects. Improved Early Results Combined with Analysis of Late Functional Status." J thorac Cardiovasc Surg. May 1990;99(5):798-808.

Salati et al. "Severe Diastolic Dysfunction After Endoventriculoplasty." J Thorac Cardiovasc Surg. Apr. 1995;109(4):694-701.

Yacoub et al. "Anatomic Correction of the Syndrome of Prolapsing Right Coronary Aortic Cusp, Dilatation of the Sinus of Valsalva , and Ventricular Septal Defect." J thorac Cardiovasc Surg. Feb. 1997;113(2):253-60.

Davila et al. "Circumferential Suture of the Mitral Ring: A Method for the Surgical Correction of Mitral Insufficiency." Journal of Thoracic Surgery Nov. 1955; 30(5): 531-60.

(56) References Cited

OTHER PUBLICATIONS

Harken et al. "The Surgical Correction of Mitral Insufficiency" Journal of Thoracic Surgery. Dec. 1954; 28(6):604-24.
Kuykendall et al. "Surgical Correction of Chronic Mitral Insufficiency in Dogs." Surgery. Oct. 1958; 44(4):718-25.
Harken et al. "The Surgical Correction of Mitral Insufficiency." Surgical Forum 4:4-7 1953.
Davila et al. "A Method for the Surgical Correction of Mitral Insufficiency." Surgery, Gynecology and Obstetrics Apr. 1954; 98(4):407-12.
Davila et al. "The Clinical and Physiologic Criteria for Surgical Correction of Mitral Insufficiency." Journal of Thoracic Surgery Feb. 1958; 35(2):206-31.
Glover et al. "The Treatment of Mitral Insufficiency by the Purse-String Technique." Journal of Thoracic Surgery Jan. 1957; 33(1): 75-101.
Rankin et al. "A Clinical Comparison of Mitral Valve Repair Versus Valve Replacement in Ischemic Mitral Regurgitation." J Thorac Cardiovasc Surg. Feb. 1988; 95(2):165-77.
Barnard et al. "A Surgical Approach to Mitral Insufficiency." Br J Surg. May 1961; 48:655-62.
McKenzie et al. "Current Concepts in Surgical Correction of Acquired Mitral Insufficiency." Circulation. Oct. 1963; 28:603-16.
Saab et al. "Left Ventricular Aneurysm: A New Surgical Approach." Thorac Cardiovasc Surg. Feb. 1989; 37(1):11-9.
Cicek et al. "Left Ventricular Endoaneurysmorrhaphy: Effect on Left Ventricular Size, Shape and Function." Cardiology. Jul.-Aug. 1997; 88(4):340-5.
Liedtke et al. "Functional Reductions in Left Ventricular Volume." J Thorac Cardiovasc Surg. Feb. 1976; 71(2):195-206.
Sosa et al. "Recurrent Ventricular Tachycardia Associated With Postinfarction Aneurysm. Results of Left Ventricular Reconstruction." J Thorac Cardiovasc Surg. May 1992; 103(5); 855-60.
Cooley, "Repair of Postinfarction Ventricular Septal Defect." J Card Surg. Jul. 1994; 9(4):427-9.
Jatene, "Left Ventricular Aneurysmectomy. Resection or Reconstruction." J Thorqc Cardiovasc Surg 1985; 89:321-31.
Bailey, et al. "Surgical Repair of Mitral Insufficiency." Diseases of the Chest, vol. XIX , No. 2, Feb. 1951, 125-137.

Henderson, et al., "The Surgical Treatment of Mitral Insufficiency." Experimental Use of Transplanted Pericardium in Dogs. Surgery 33(6):858-868; 1953.
Sakakibara, "A Surgical Approach to the Correction of Mitral Insufficiency." Annals of Surgery. vol. 142, No. 2, Aug. 1955, 196-203.
Harken et al. "The Surgical Correction of Mitral Insufficiency." The Journal of Thoracic Surgery. 28(6):604-627., 1954.
Bailey et al. "The Surgical Correction of Mitral Insufficiency by the Use of Pericardial Grafts." The Journal of Thoracic Surgery, vol. 28, No. 6, Dec. 1954, 551-603.
Kay et al. "Surgical Treatment of Mitral Insufficiency." Surgery. vol. 37, No. 5. May 1955, 697-706.
Templeton III, et al. "Experimental Reconstruction of Cardiac Valves by Venous and Pericardial Grafts." Annals of Surgery vol. 129, No. 2, Feb. 1949, 161-176.
Moore et al. "Unsuitability of Transventricular Autogenous Slings for Diminishing Valvular Insufficiency." Surgery, vol. 33, No. 2, Feb. 1953, 173-182.
Murray et al. "Reconstruction of the Valves of the Heart." The Canadian Medical Association Journal, vol. 38, No. 4, Apr. 1938, 317-319.
Bolling et al. "Early Outcome of Mitral Valve Reconstruction in Patients With End-Stage Cardiomyopathy." J Thorac Cardiovasc Surg 1995; 109:676-683.
Kameda et al. "Annuloplasty for Severe Mitral Regurgitation Due to Dilated Cardiomyopathy." Ann Thorac Surg 1996; 61:1829-1832.
Bolling et al. "Intermediate-Term Outcome of Mitral Reconstruction in Cardiomyopathy." Journal of Thoracic Cardiovascular Surgery, vol. 115, No. 2, Feb. 1998, 381-388.
Harlan et al. Manual of Cardiac Surgery, vol. 2, 1981 Figs. 16.3-16.4.
Edmunds, Jr. et al. "Septal Defect." Atlas of Cardiothoracic Surgery 1990.
Koniaris, MD et al. "Dynamic Retention: A Technique for Closure of the Complex Abdomen in Critically Ill Patients." Archives of Surgery, vol. 136, No. 12, Dec. 2001, 1359-1362.
Fucci et al. "Improved Results With Mitral Valve Repair Using New Surgical Techniques." European Journal of Cardio-Thoracic Surgery, vol. 9, 1995, 621-626.

* cited by examiner

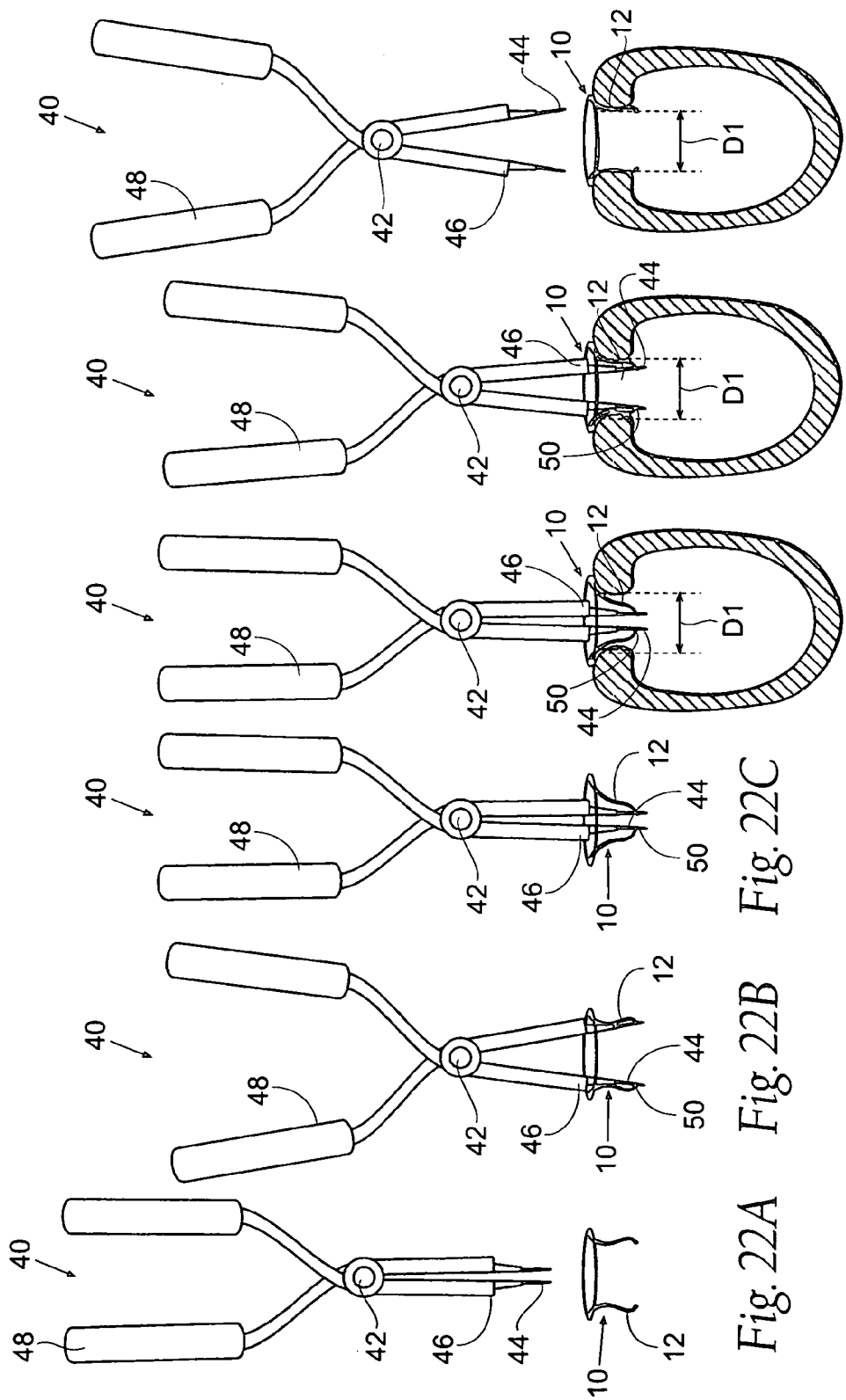

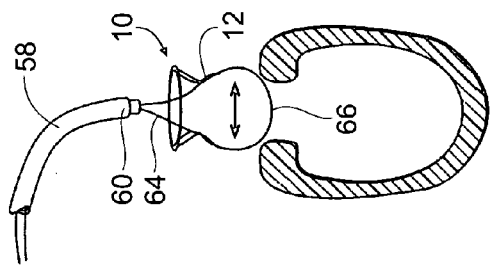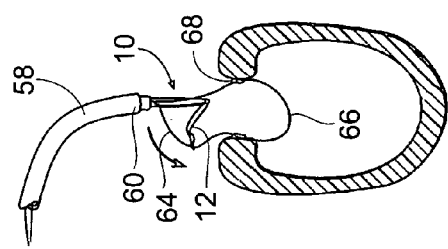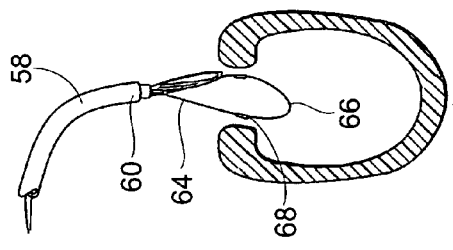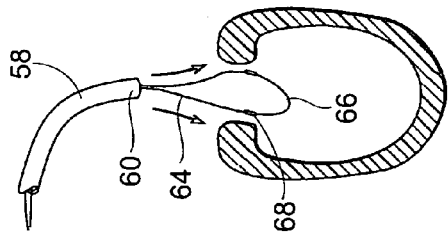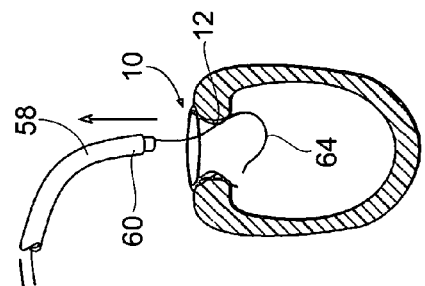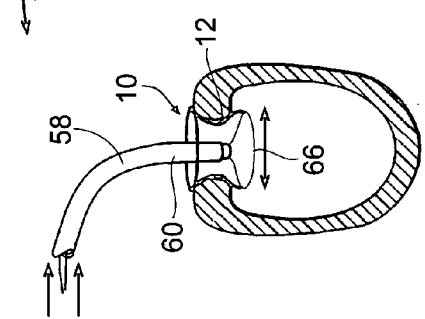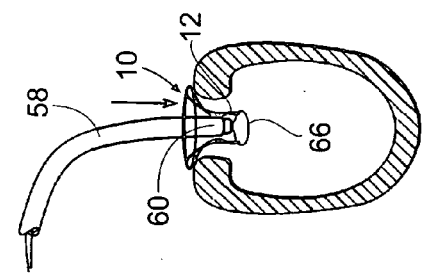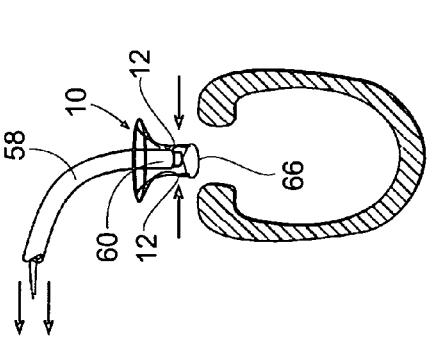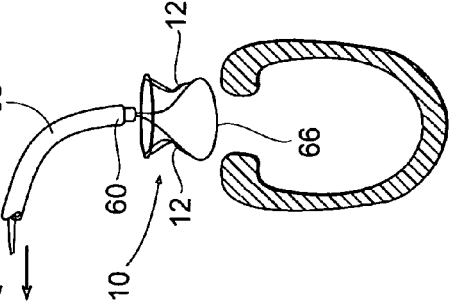

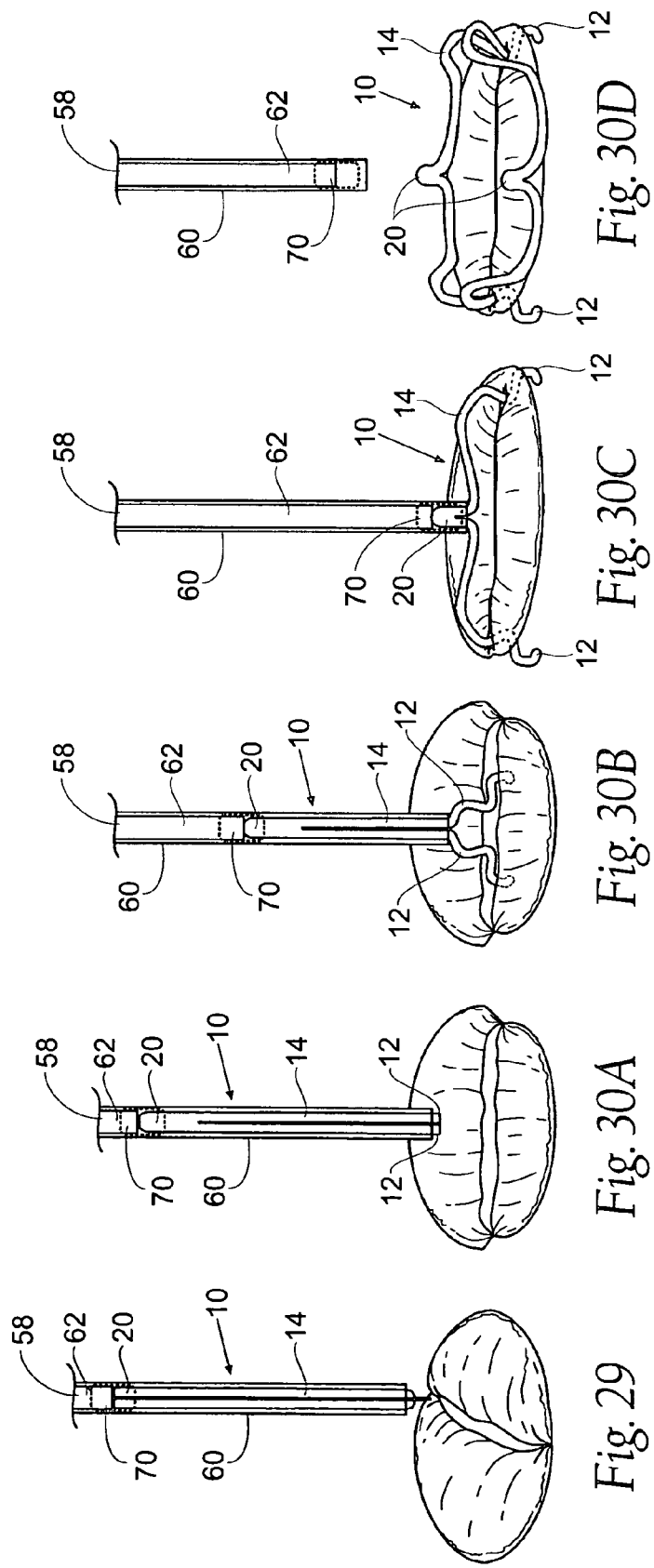

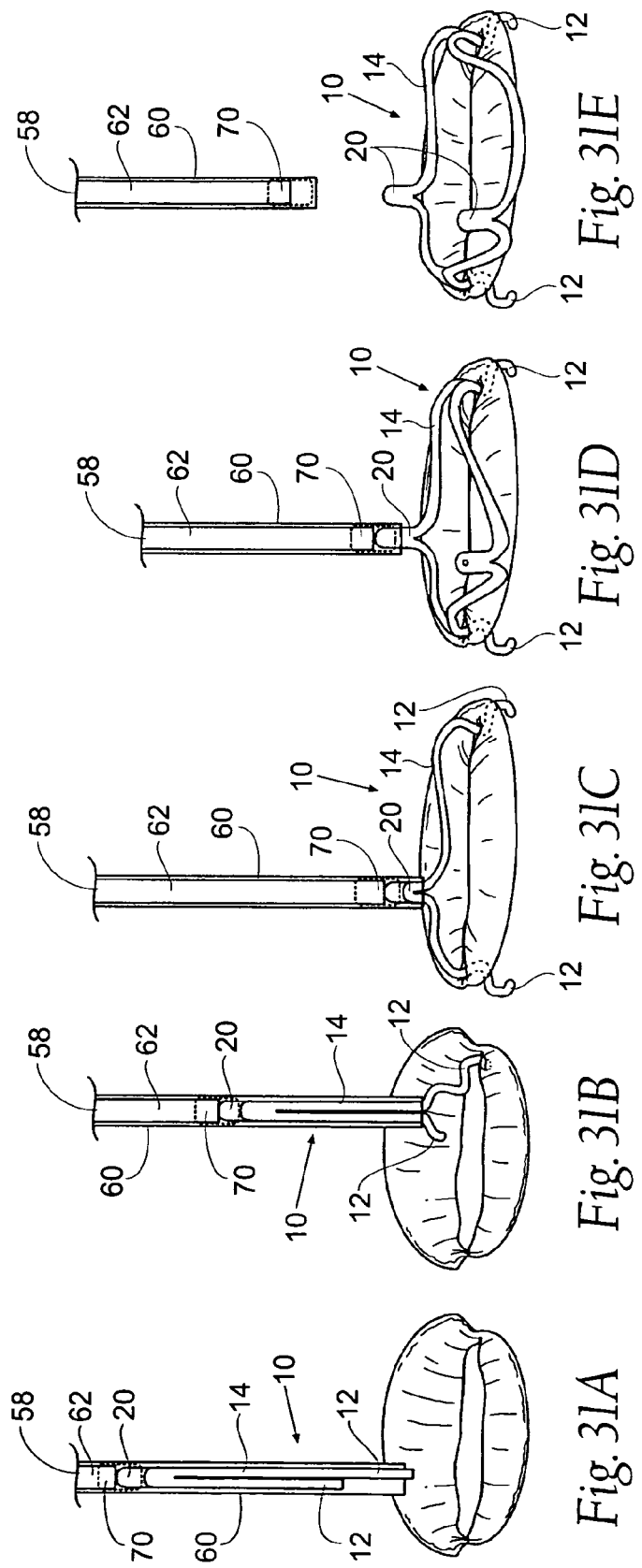

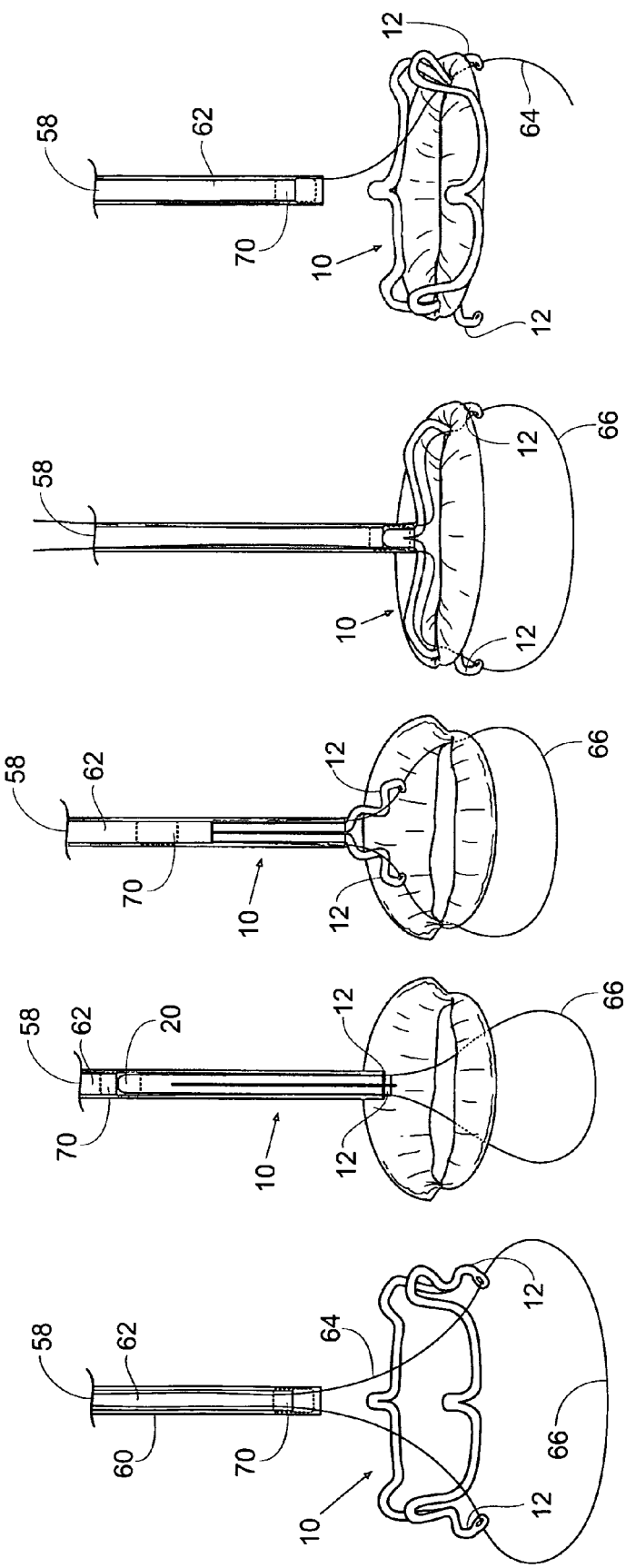

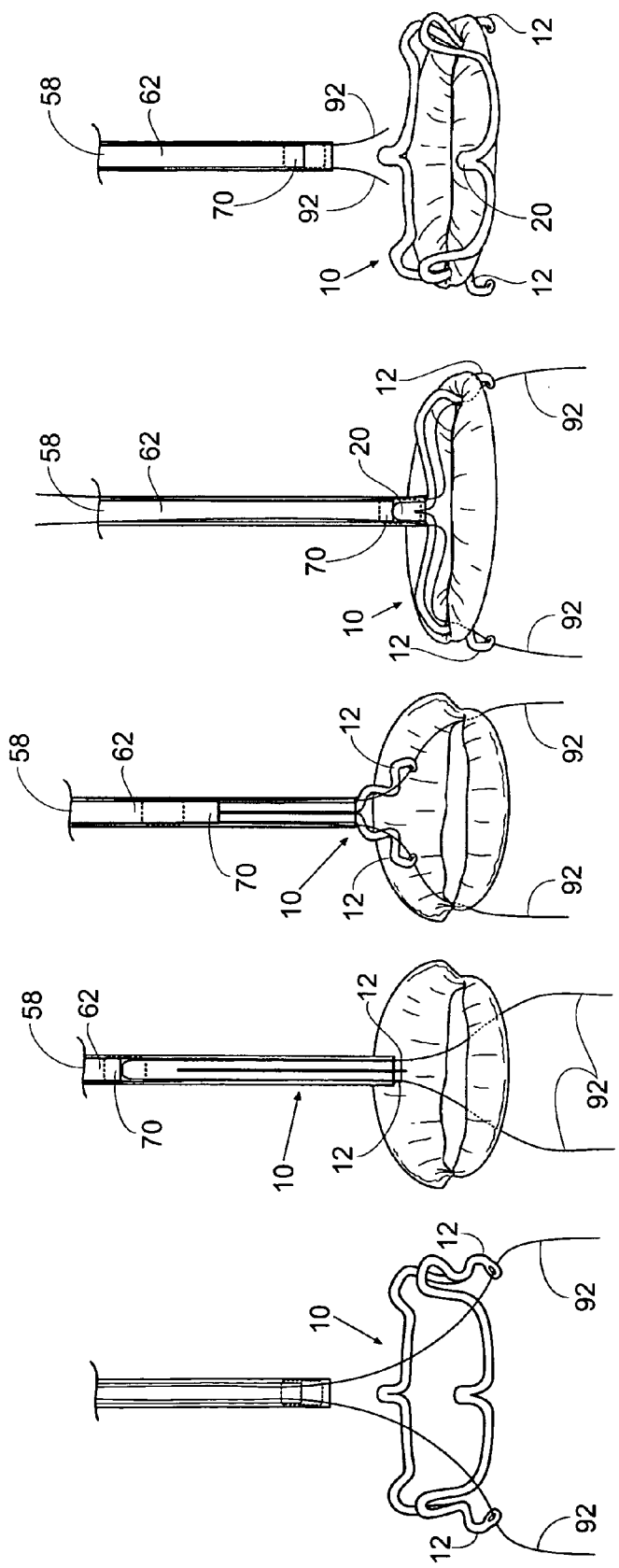

DEVICES, SYSTEMS, AND METHODS FOR RESHAPING A HEART VALVE ANNULUS

RELATED APPLICATIONS

This application is a continuation of U.S. patent application Ser. No. 10/677,104, filed Oct. 1, 2003, and claims the benefit of U.S. Provisional Application Ser. No. 60/429,444, filed Nov. 26, 2002, and entitled "Heart Valve Remodeling Devices".

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called diastole. The cycle ends with a period of ventricular contraction, called systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atria into the corresponding ventricles. Shortly after systole (i.e., ventricular emptying) begins, the tricuspid and mitral valves close (see FIG. 3)—to prevent back flow from the ventricles into the corresponding atria—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

The mitral and tricuspid valves are defined by fibrous rings of collagen, each called an annulus, which forms a part of the fibrous skeleton of the heart. The annulus provides attachments for the two cusps or leaflets of the mitral valve (called the anterior and posterior cusps) and the three cusps or leaflets of the tricuspid valve. The leaflets receive chordae tendinae from more than one papillary muscle. In a healthy heart, these muscles and their tendinous cords support the mitral and tricuspid valves, allowing the leaflets to resist the high pressure developed during contractions (pumping) of the left and right ventricles.

In a healthy heart, the chordae tendinea become taut, preventing the leaflets from being forced into the left or right atria and everted. Prolapse is a term used to describe this condition. This is normally prevented by contraction of the papillary muscles within the ventricle, which are connected to the mitral valve leaflets by the chordae tendineae. Contraction of the papillary muscles is simultaneous with the contraction of the ventricle and serves to keep healthy valve leaflets tightly shut at peak contraction pressures exerted by the ventricle.

II. Characteristics and Causes of Mitral Valve Dysfunction

In a healthy heart (see FIG. 4), the dimensions of the mitral valve annulus—when measured septal (S)-to-lateral (L), as well as from posterior commissure CP to anterior commissure CA—create an anatomic shape and tension such that the leaflets coapt, forming a tight junction, at peak contraction pressures. Where the leaflets coapt at the opposing medial and laterial sides of the annulus are called the leaflet commissures, and are designated in FIG. 4 and in other Figures as CP (denoting the posterior commissure) and CA (denoting the anterior commissure).

Valve malfunction can result from the chordae tendinea (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease.

Regardless of the cause (see FIG. 5), mitral valve dysfunction can occur when the leaflets do not coapt at peak contraction pressures. As FIG. 5 shows, the coaptation line of the two leaflets is not tight at systole. As a result, an undesired back flow of blood from the left ventricle into the left atrium can occur. This condition is called regurgitation.

In some cases (see FIG. 6), the leaflets do not form a tight coaptation junction because the dimensions of the mitral valve annulus, measured from commissure to commissure—CP to CA—and/or septal to lateral—S to L—change. The changed dimensions no longer create the anatomic shape and tension in which the leaflets coapt at peak contraction pressures.

Comparing a healthy annulus in FIG. 4 to an unhealthy annulus in FIG. 6, the unhealthy annulus is dilated and, in particular, the septal-to-lateral distance is increased. As a result, the shape and tension defined by the annulus becomes less oval (see FIG. 4) and more round (see FIG. 6). This condition is called dilation. When the annulus is dilated, the shape and tension conducive for coaptation at peak contraction pressures progressively deteriorate. Instead, at peak contraction pressures, the leaflets do not coapt completely, and a gap forms between the leaflets. During systole, regurgitation can occur through this gap. It is believed that the ratio between the commissure distance and septal-to-lateral distance bears a relationship to the effectiveness of leaflet coaptation. If the septal-to-lateral distance increases, the ratio changes, and when the ratio reaches a certain value, regurgitation or the likelihood of regurgitation is indicated.

As a result of regurgitation, "extra" blood back flows into the left atrium. During subsequent diastole (when the heart relaxes), this "extra" blood returns to the left ventricle, creating a volume overload, i.e., too much blood in the left ventricle. During subsequent systole (when the heart contracts), there is more blood in the ventricle than expected. This means that: (1) the heart must pump harder to move the extra blood; (2) too little blood may move from the heart to the rest of the body; and (3) over time, the left ventricle may begin to stretch and enlarge to accommodate the larger volume of blood, and the left ventricle may become weaker.

Although mild cases of mitral valve regurgitation result in few problems, more severe and chronic cases eventually weaken the heart and can result in heart failure. Mitral valve regurgitation can be an acute or chronic condition. It is sometimes called mitral insufficiency.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

To date, invasive, open heart surgical approaches have been used to repair mitral valve dysfunction. During these surgical repair procedures, efforts are made to cinch or resect portions and/or fix in position large portions of the dilated annulus. During these surgical repair procedures, the annulus can be reshaped with annular or peri-annular rings or similar ring-like devices. The repair devices are typically secured to the annulus and surrounding tissue with suture-based fixation. The repair devices extend over the top and over much or all of the circumference of the annulus and leaflet surfaces.

A physician may decide to replace an unhealthy mitral valve rather than repair it. Invasive, open heart surgical approaches are used to replace the natural valve with either a mechanical valve or biological tissue (bioprosthetic) taken from pigs, cows, or horses.

The need remains for simple, cost-effective, and less invasive devices, systems, and methods for treating dysfunction of a heart valve, e.g., in the treatment of mitral valve regurgitation.

SUMMARY OF THE INVENTION

The invention provides devices, systems and methods that reshape a valve annulus. The devices, systems, and methods include an implant that is sized and configured to rest near or within the leaflet commissures of a heart valve annulus. In use, the implant contacts and outwardly displaces tissue to reshape the heart valve annulus. The implant, in use, may restore to the heart valve annulus and leaflets a more effective anatomic shape and tension. The more normal anatomic shape and tension are conducive to coaptation of the leaflets during systole, which, in turn, reduces regurgitation. The implant restores function to the valve, without surgically cinching, resecting, and/or fixing in position large portions of a dilated annulus, or without the surgical fixation of ring-like structures.

Other features and advantages of the invention shall be apparent based upon the accompanying description, drawings, and claims.

DESCRIPTION OF THE DRAWINGS

FIGS. 22A to 22F diagrammatically show a method of using the tool shown in FIG. 21 to install an elastic implant in a valve annulus to reshape the annulus and restore leaflet coaptation.

FIGS. 27A to 27I are diagrammatic views of a method for deploying an elastic implant of the type shown in FIG. 10 into a valve annulus with the aid of a guide wire loop to reshape the annulus and restore leaflet coaptation.

FIG. 29 is a side view of the distal end of the implant delivery catheter of the type shown in FIG. 23C, showing a symmetrical foldable elastic implant of the type shown in FIG. 15A folded and collapsed in a sleeve for deployment into the left atrium in the manner shown in FIGS. 23A to 23C.

FIGS. 30A to 30D are diagrammatic views of a method for manipulating the distal end of the implant delivery catheter shown in FIG. 29 to deploy a symmetrically folded and collapsed elastic implant of the type shown in FIG. 15A into a valve annulus to reshape the annulus and restore leaflet coaptation.

FIGS. 31A to 31E are diagrammatic views of a method for manipulating the distal end of the implant delivery catheter shown in FIG. 29 to deploy an asymmetrically folded and collapsed elastic implant of the type shown in FIG. 15D into a valve annulus to reshape the annulus and restore leaflet coaptation.

FIG. 32 is a side view of the distal end of the implant delivery catheter of the type shown in FIG. 23C, showing a symmetrical foldable elastic implant of the type shown in FIG. 15A tethered to a guide wire loop to aid in its implantation into a valve annulus to reshape the annulus and restore leaflet coaptation.

FIGS. 33A to 33D are diagrammatic views of a method for manipulating the distal end of the implant delivery catheter shown in FIG. 32 to deploy a symmetrically folded and collapsed elastic implant of the type shown in FIG. 15A into a valve annulus with the aid of a guide wire loop to reshape the annulus and restore leaflet coaptation.

FIGS. 35 and 36A to 36D are diagrammatic views of a method for manipulating the distal end of the implant delivery catheter to deploy a symmetrically folded and collapsed elastic implant of the type shown in FIG. 15A into a valve annulus with the aid of a separate guide wires to reshape the annulus and restore leaflet coaptation.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Implants for Reshaping a Heart Valve Annulus

A. Overview

Figure 1:
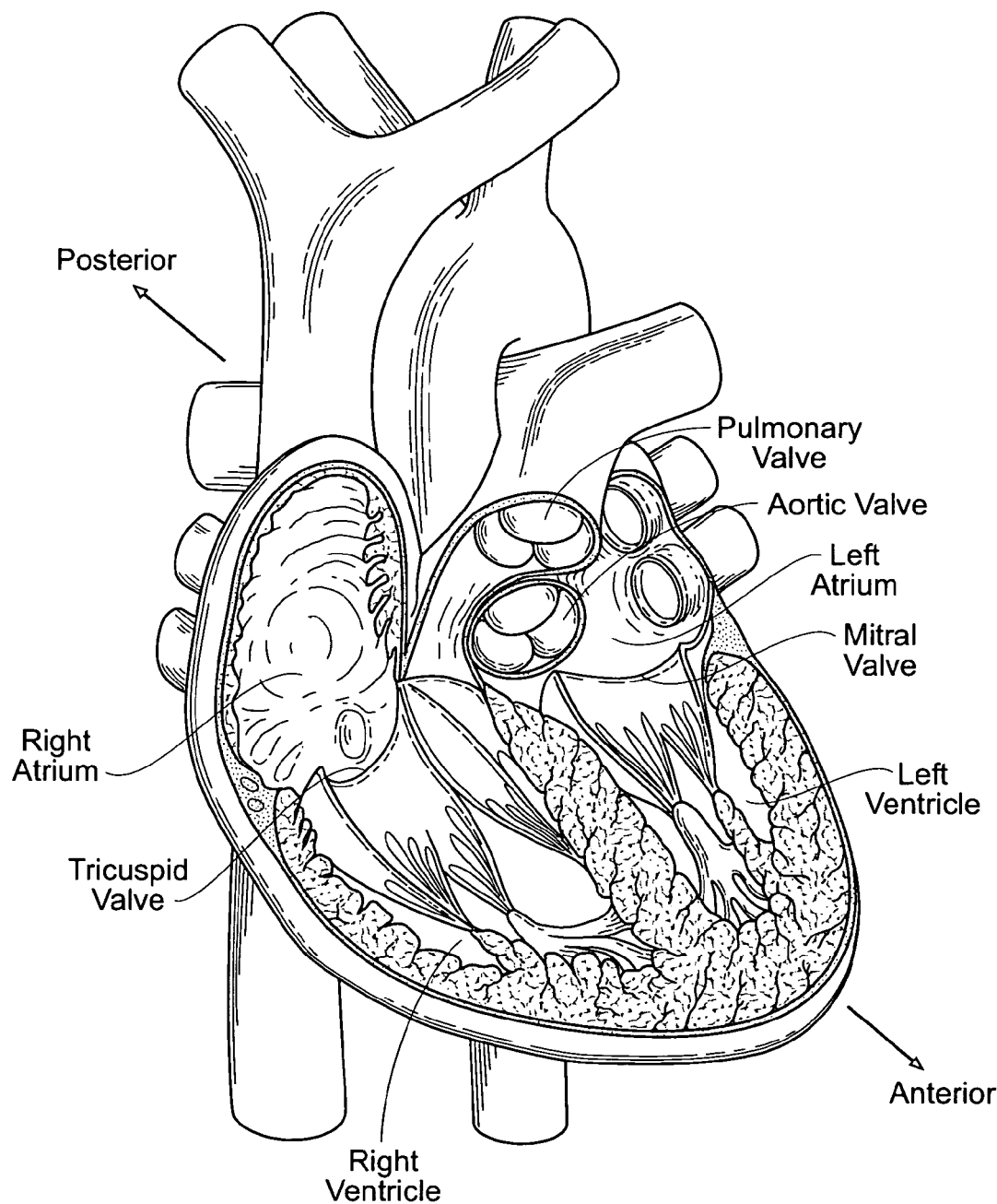
FIG. 1 is a perspective, anterior anatomic view of the interior of a healthy heart.
Figure 2:
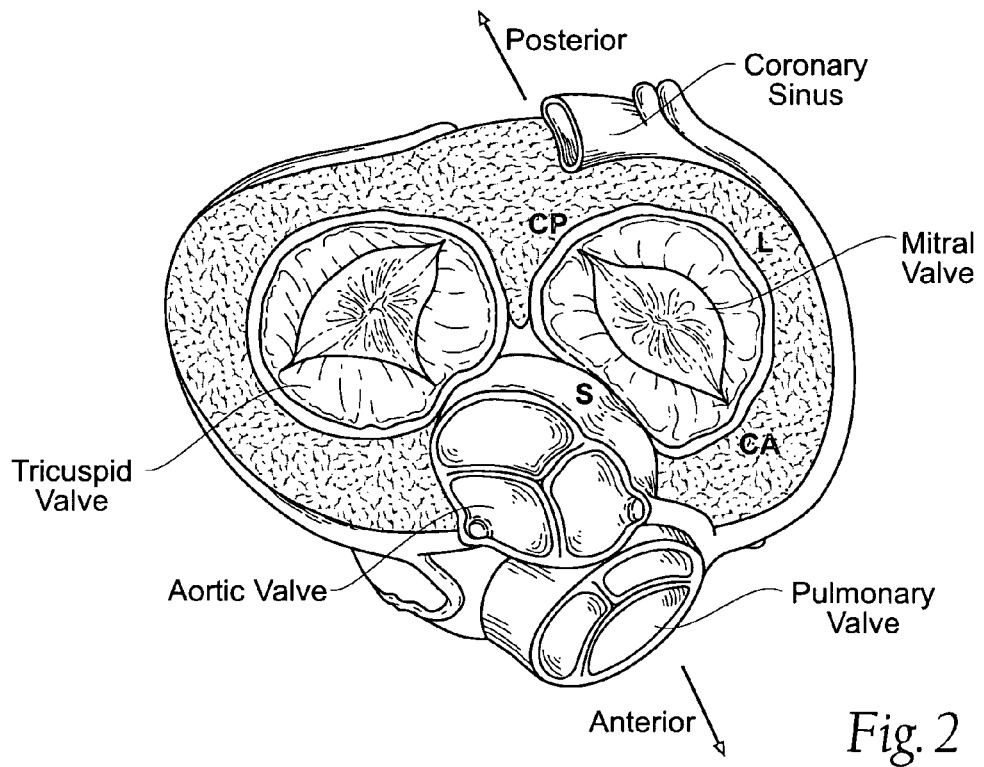
FIG. 2 is a superior anatomic view of the interior of a healthy heart, with the atria removed, showing the condition of the heart valves during diastole.
Figure 3:
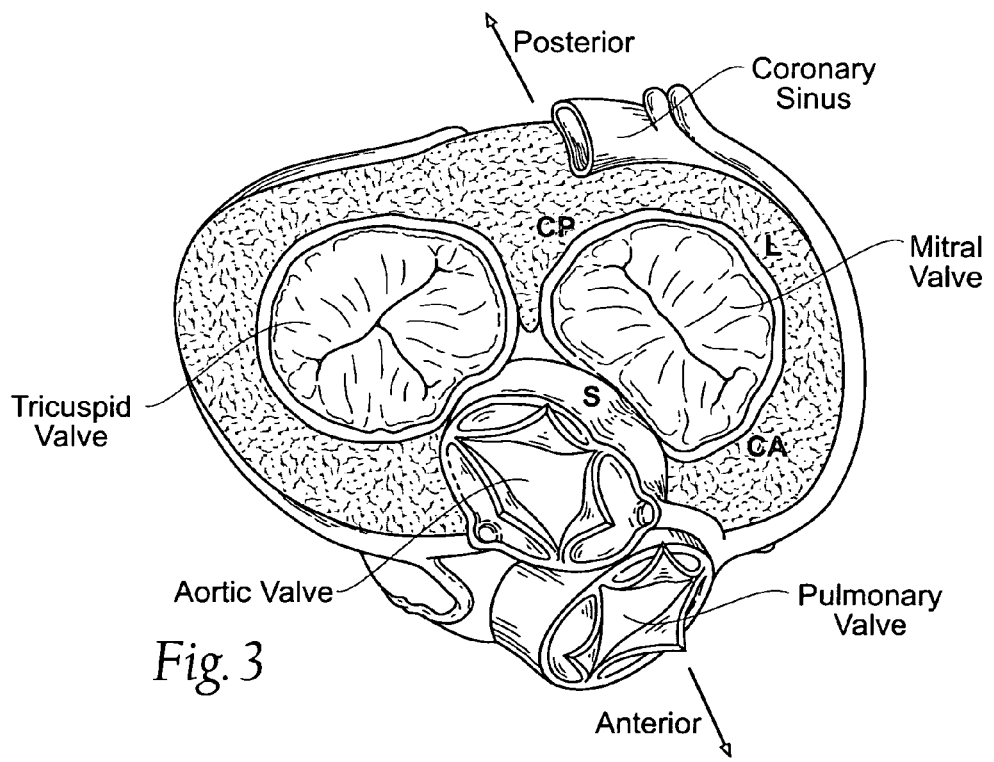
FIG. 3 is a superior anatomic view of the interior of a healthy heart, with the atria removed, showing the condition of the heart valves during systole.
Figure 4:
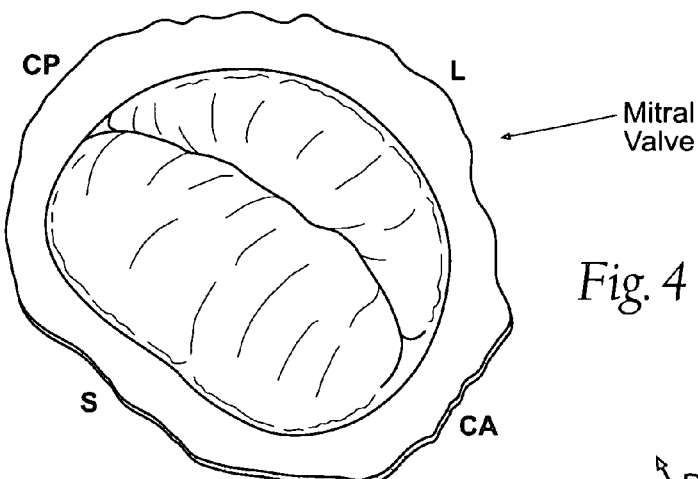
FIG. 4 is a superior anatomic view of a healthy mitral valve during systole, showing the leaflets properly coapting.
Figure 5:
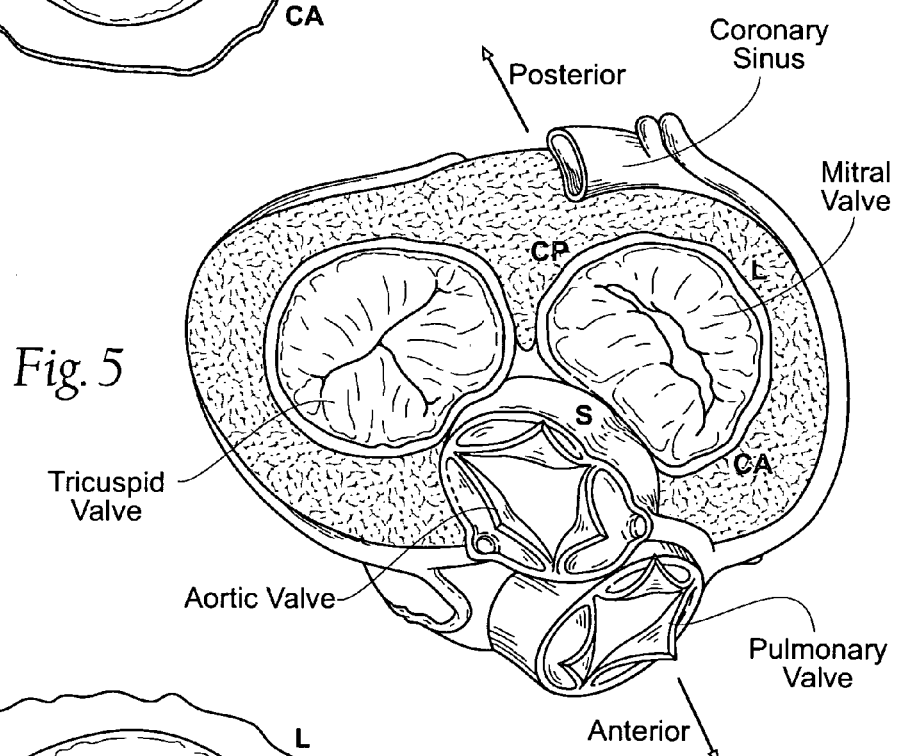
FIG. 5 is a superior anatomic view of the interior of a heart, with the atria removed, showing the condition of the heart valves during systole, and further showing a dysfunctional mitral valve in which the leaflets are not properly coapting, causing regurgitation.
Figure 6:
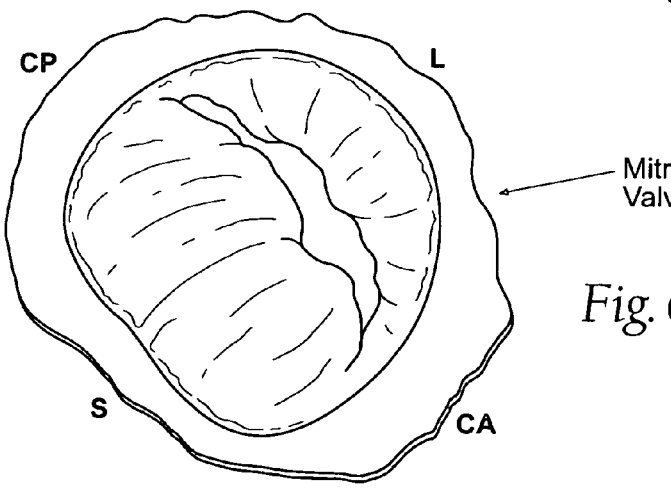
FIG. 6 is a superior anatomic view of a disfunctional mitral valve during systole, showing that the leaflets are not properly coapting, causing regurgitation.
Figure 7A:
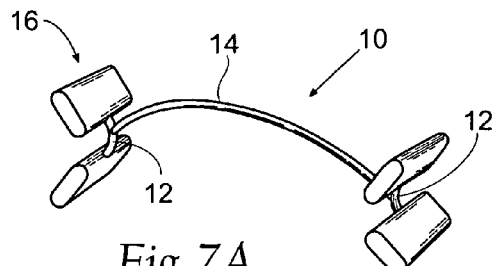
FIG. 7A is a side perspective view of an elastic implant sized and configured to rest within or near the leaflet commissures of a dysfunctional heart valve annulus to reshape the annulus and improve leaflet coaptation.
Figure 8:
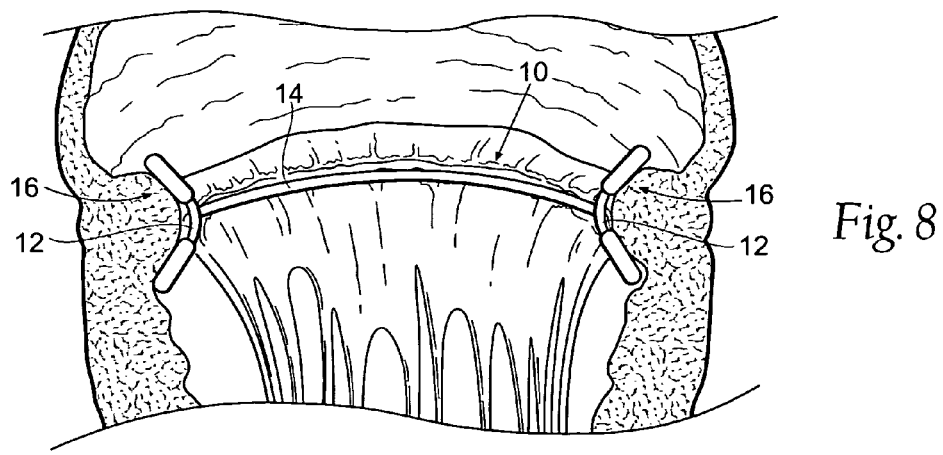
FIG. 8 is a side anterior anatomic view of a mitral valve annulus in which the elastic implant shown in FIG. 7A has been implanted.

FIGS. 7A and 8 show an implant 10 sized and configured to rest within or near a heart valve annulus. In use, the implant is shown in a mitral valve, and, in this arrangement, extends along the major (i.e., longest) axis above and/or along the valve annulus. The implant 10 is sized and shaped so that, in use, it applies a mechanical force along the major axis. The mechanical force serves to outwardly displace tissue (i.e., to displace tissue away from the center of the annulus) to reshape the annulus. In the illustrated embodiment (on the mitral valve), the mechanical force serves to lengthen the long axis of the annulus and, in doing so, can reactively shorten in the minor (i.e. shortest) axis, as well as correspondingly reshape other surrounding anatomic structures. It should be appreciated that, when situated in other valve structures, the axes affected may not be the "major" and "minor" axes, due to the surrounding anatomy.

Figure 9:
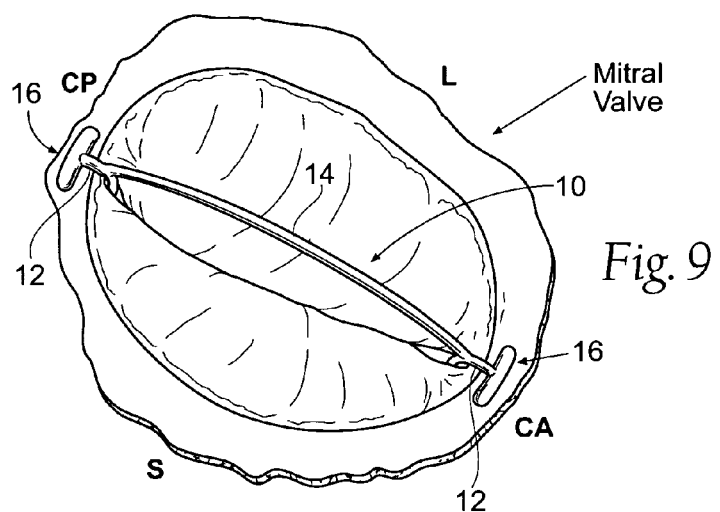
FIG. 9 is a superior anatomic view of a mitral valve in which the elastic implant shown in FIG. 7A has been implanted, showing the implant stretching the commissures to restore leaflet coaptation.

The mechanical force applied by the implant 10 restores to the heart valve annulus and leaflets a more normal anatomic shape and tension (see FIG. 9). The more normal anatomic shape and tension are conducive to coaptation of the leaflets during systole, which, in turn, reduces regurgitation. The implant 10 restores normal function to the valve, without surgically cinching, resecting, and/or fixing in position large portions of a dilated annulus or leaflets, or without the surgical fixation of ring-like structures.

As will be described in greater detail later, the implant 10 lends itself to delivery to a targeted heart valve site by catheter-based, intravascular techniques, under image guidance. Image guidance includes but is not limited to fluoroscopy, ultrasound, magnetic resonance, computed tomography, or combinations thereof. Alternatively, the implant 10 can be delivered using conventional open heart surgical techniques or by thorascopic surgery techniques.

In its most basic form, the implant 10 is made—e.g., by bending, shaping, joining, machining, molding, or extrusion—from a biocompatible metallic or polymer material, or a metallic or polymer material that is suitably coated, impregnated, or otherwise treated with a material to impart biocompatibility, or a combination of such materials. The material is also desirably radio-opaque to facilitate fluoroscopic visualization.

As FIG. 7A shows, the implant 10 includes a pair of struts 12 joined by an intermediate rail 14. As FIG. 8 shows, the struts 12 are sized and configured to rest at or near the leaflet commissures. It should be appreciated that the leaflet commissures may not, and typically are not, situated at geometrically opposite sides of the annulus (although for the purpose of illustration, they are shown that way in the Figures). The position of the struts 12 can be selected to conform to an asymmetric morphology of the annulus, as is later described in connection with FIGS. 13A and 13B.

The rail 14 spans the struts 12. The rail 14 (like the struts 12) can take various shapes and have various cross-sectional geometries. The rail 14 (and/or the struts 12) can have, e.g., a generally curvilinear (i.e., round or oval) cross-section, or a generally rectilinear cross section (i.e., square or rectangular), or combinations thereof.

In FIGS. 7A and 8, the implant is "elastic." The rail 14 is sized and configured to possess a normal, unloaded, shape or condition (shown in FIG. 7A), in which the rail 14 is not in compression and the struts 12 are spaced apart farther than the anterior commissure to posterior commissure dimension of the targeted heart valve annulus. The material of the implant is selected to possess a desired spring constant. The spring constant imparts to the rail 14 the ability to be elastically compressed out of its normal, at rest condition, in response to external compression forces applied at the struts. The rail 14 is sized and configured to assume an elastically loaded, in compression condition, during which the struts 12 are spaced apart a sufficiently shorter distance to rest in engagement with tissue at or near the leaflet commissures (see FIG. 8).

When in its elastically loaded, compressed condition (see FIG. 9), the rail 14 exerts opposing forces to the tissues at or near the commissures through the struts 12, tending to outwardly displace tissue and stretch the annulus along its major axis, which also typically stretches apart the leaflet commissures, shortens the minor axis, and/or reshapes surrounding anatomic structures. The implant thereby reshapes the valve annulus toward a shape more conducive to leaflet coaptation.

An elastic implant can be made, e.g., from superelastic alloy, such that the implant can be elastically straightened and/or folded to fit within a catheter or sheath during deployment, and will regain its shape upon deployment (this characteristic will be described in greater detail later).

Desirably, the elasticity of the implant 10 itself, along with the elasticity of the valve tissue, ensure that the implant 10 can be positioned in the valve under a state of net compression and thus remain anchored without the use of sutures, adhesives, or other fixation materials, i.e. which is called compressive anchoring. The implant 10 may itself deform elastically, although not necessarily so, but the characteristic of the implant 10 being elastically deformable may help to maintain compressive anchoring. If the implant 10 does not deform elastically or does so only slightly, the implant 10 relies on tissue elasticity to keep the implant anchored.

As FIGS. 7A to 7E and 8 show, and as will be described in greater detail later, the struts 12 may carry other structures or mechanisms 16 to further enhance the anchorage and stabilization of the implant in the heart valve annulus. The mechanisms 16 may be located below the plane of the annulus, to engage infra-annular heart tissue adjoining the annulus in the ventricle, and/or be located at or above the plane of the annulus, to engage tissue on the annulus or in the atrium.

The spring constant of the implant may be selected to be greater than the spring constant of adjoining tissue. Alternatively, the spring constant of the implant may be selected to approximate the spring constant of adjoining tissue, thereby providing compliance to allow the implant 10 to adapt to tissue morphology during use. The spring constant of the implant 10 may vary along the length of the rail 14, so that some portions of the rail 14 are stiffer or more compliant than other portions of the rail 14.

In an alternative arrangement, the implant 10 may be formed from a plastically deformable material. In this embodiment, the implant 10 is manufactured in a normally collapsed condition. The implant 10 is expanded in situ into an in use condition within the annulus, e.g., by an inflatable body (e.g., balloon) or by a suitable mechanical device (e.g., a scissorjack). The use and deployment of a plastically deformable implant will be described in greater detail later, after the structure, deployment, and use of elastic implants are described.

B. Illustrative Elastic Implant Configurations

An elastic implant 10 having the characteristic just described can take various forms and configurations. The following describes various illustrative arrangements.

(i) Collapsible Annular Implants

Figure 7B:
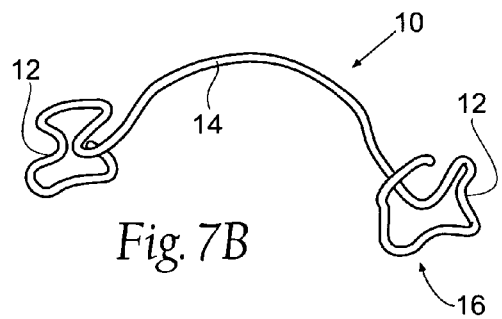
FIGS. 7B to 7E are side perspective views of illustrative alternative configurations of the elastic implant shown in FIG. 7A.
Figure 7C:
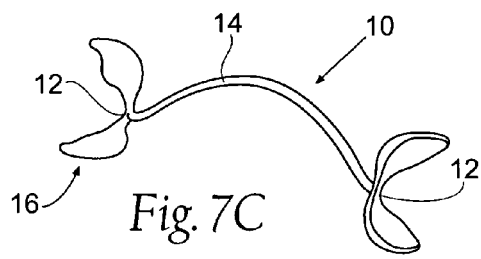
Figure 7D:
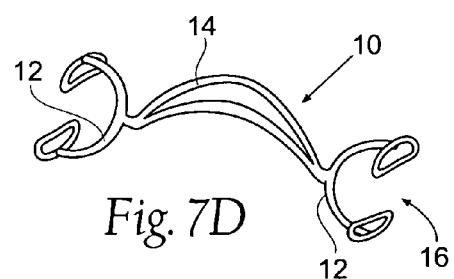
Figure 7E:
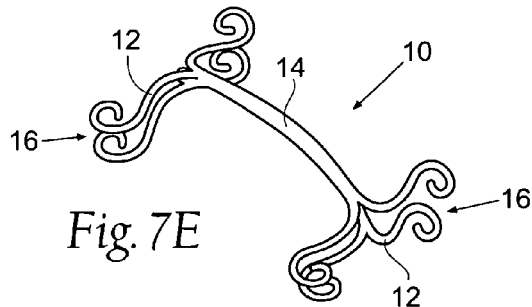
Figure 10:
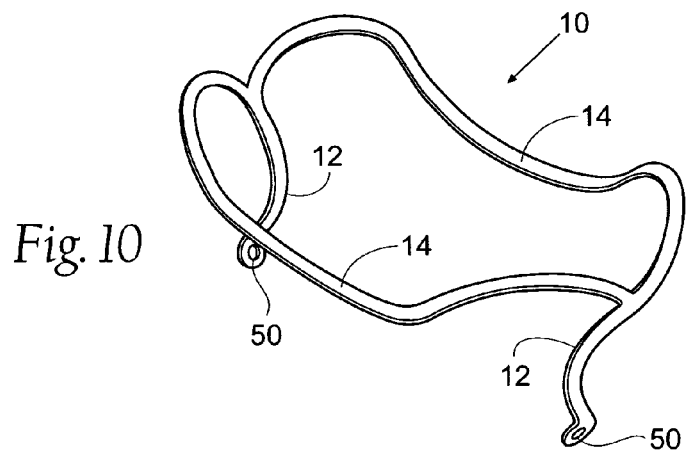
FIG. 10 is a side perspective view of another embodiment of an elastic implant sized and configured to rest within or near the leaflet commissures of a dysfunctional heart valve annulus to reshape the annulus and restore leaflet coaptation, the implant defining a closed annular structure.

The implants 10 in FIGS. 7A to 7C comprise a single rail 14 spanning the distance between the struts 12. As shown in FIGS. 7D and 10, an implant 10 can include more than a single rail 14, imparting a normally closed, annular shape to the implant. As will be described in greater detail later, an implant 10 of this type can be conveyed to an implantation site, e.g., within a catheter or sheath, in a collapsed, straightened condition (with the rails 14 collapsed side-by-side). When deployed from the catheter or sheath, the implant 10 springs open to assume the normally closed, annular shape shown in FIGS. 7D and 10.

Figure 11:
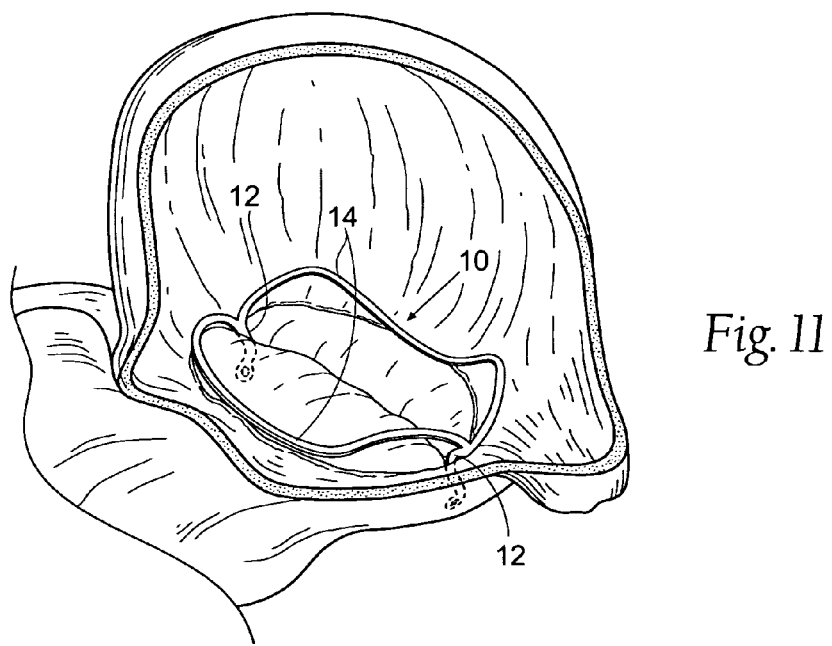
FIG. 11 is a perspective anatomic view, taken from an anterior and slightly superior viewpoint, of a mitral valve in which the elastic implant of the type shown in FIG. 10 has been implanted, showing the implant stretching the commissures to restore leaflet coaptation, and also showing the implant as hugging the annulus.
Figure 12:
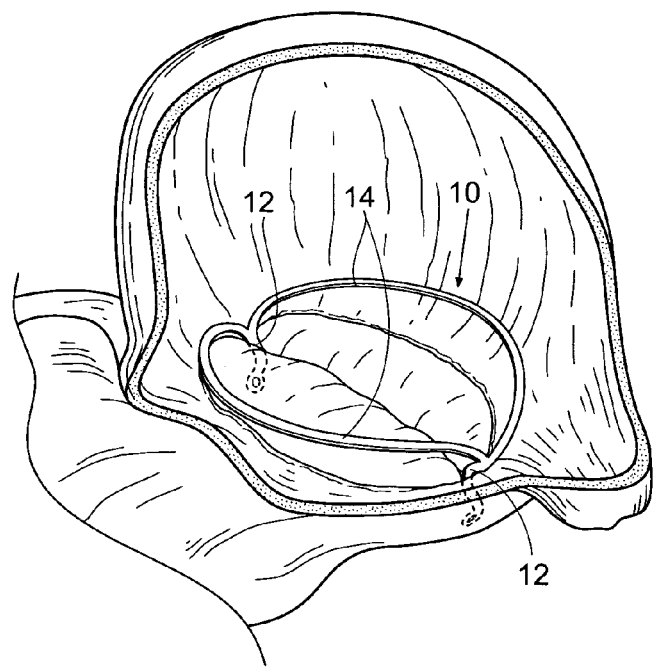
FIG. 12 is a perspective anatomic view, taken from an anterior and slightly superior viewpoint, of a mitral valve in which the elastic implant of the type shown in FIG. 10 has been implanted, showing the implant stretching the commissures to restore leaflet coaptation, and also showing the implant as rising above the annulus.
Figure 20A:
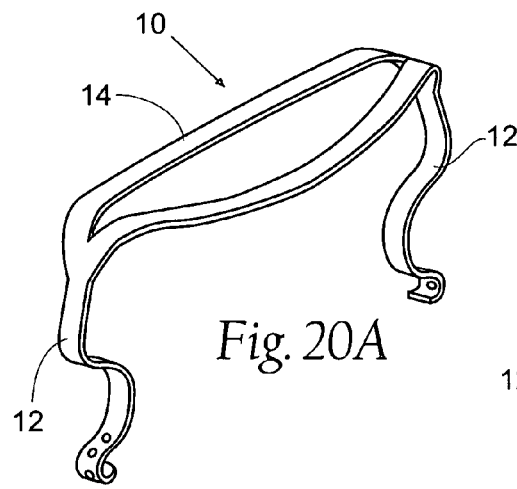
FIGS. 20A and 20B are, respectively, a side perspective view and an anatomic view (when implanted) of an elastic implant sized and configured to rest within or near the leaflet commissures of a dysfunctional heart valve annulus to reshape the annulus and restore leaflet coaptation and also showing the implant as rising significantly above the annulus.
Figure 20B:
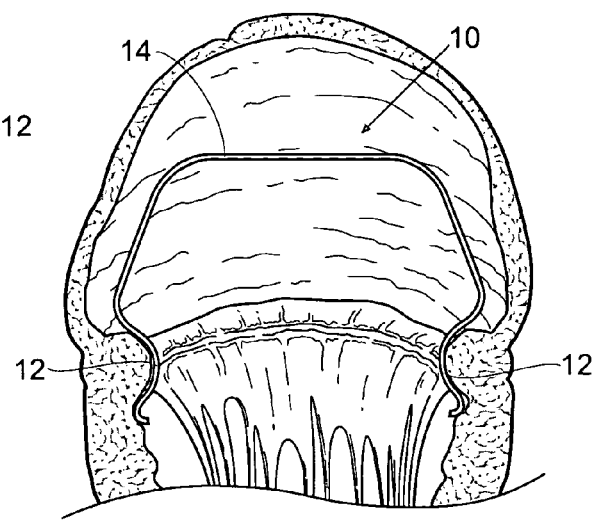
Figure 20C:
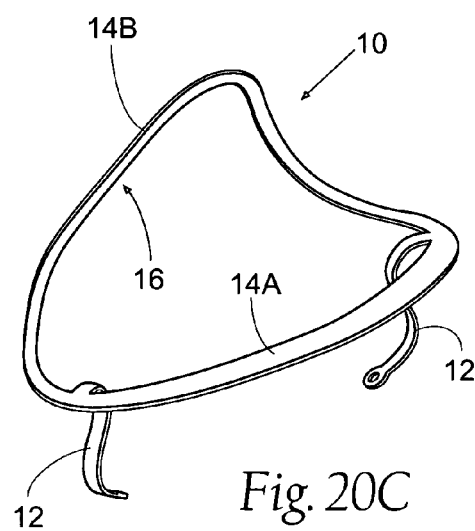
FIGS. 20C and 20D are, respectively, a side perspective view and an anatomic view (when implanted) of an elastic implant sized and configured to rest within or near the leaflet commissures of a dysfunctional heart valve annulus to reshape the annulus and restore leaflet coaptation, and showing the presence of one rail that hugs the annulus and another rail that rises above the implant to serve as a mechanism that anchors and stabilizes the implant in the annulus.
Figure 20D:
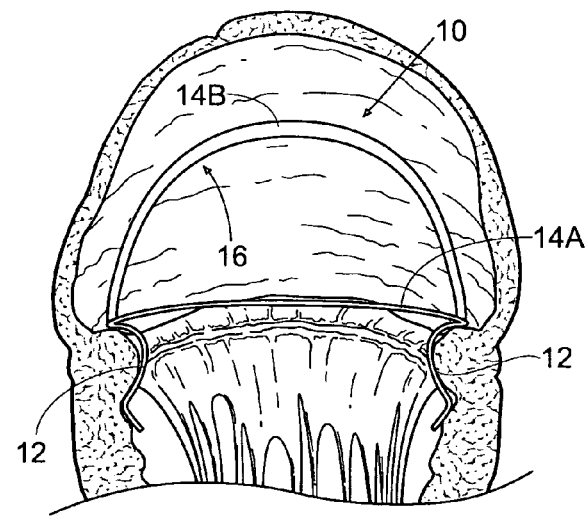

In the arrangement illustrated in FIG. 10, the implant 10 includes two rails 14 spanning the struts 12. The shape and configuration of the rails 14 can be varied, depending upon the desired orientation of the rails 14 with respect to the annulus itself. For example, in FIG. 11, the two rails 14 are shaped and configured so that, when implanted, the rails 14 follow the circumferential path of the annulus and rest in generally the same plane as the annulus. This implant can be characterized as "hugging" the annulus. In the example shown in FIG. 12, the two rails 14 are shaped and configured so that, when implanted, the rails 14 follow the circumferential path of the annulus, and also rise above the plane of the annulus. This implant 10 can be characterized as "riding above" the annulus. An implant 10 that "rides above" the annulus can extend close to the annulus (as FIG. 12 shows) or rise significantly above the annulus toward the dome of the atrium as FIGS. 20A and 20B show. As FIGS. 20C and 20D show, an implant 10 can include a rail 14A that hugs the annulus and a rail 14B that rides above the annulus and contacts a heart wall, serving as a mechanism 16 that orients and stabilizes the implant.

When the rail or rails 14 of a given implant follow the circumferential contour of the annulus, either at or above the plane of the annulus, the rails 14 rest out of the way of blood flow though the valve and may reduce hemolysis or thrombosis.

As FIGS. 13A to 13E show, the rails 14 of a given annular implant 10 can be interrupted to impart a normally open annular ("hemi") shape to the implant 10. As will be described in greater detail later, an implant 10 of this type also can be conveyed to an implantation site, e.g., within a catheter or sheath, in a collapsed, straightened condition, and then deployed to assume the open, annular shape shown in FIGS. 13A to 13E.

Figure 13A:
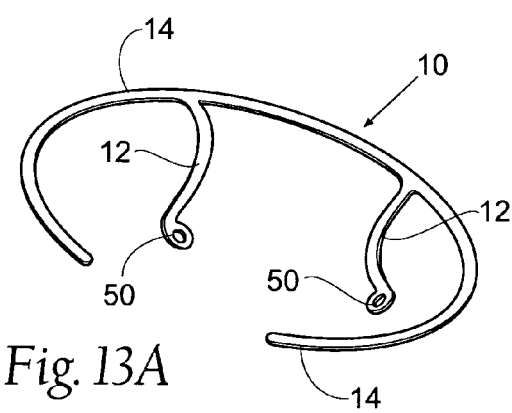
FIGS. 13A to 13C are side perspective views of illustrative embodiments of an elastic implant sized and configured to rest within or near the leaflet commissures of a dysfunctional heart valve annulus to reshape the annulus and restore leaflet coaptation, the implant defining an open annular structure.
Figure 13B:
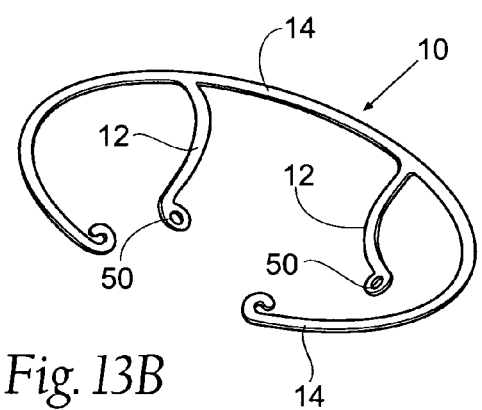
Figure 13C:
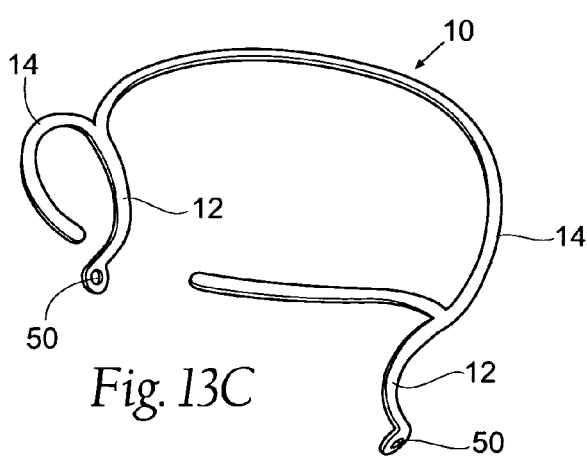
Figure 13D:
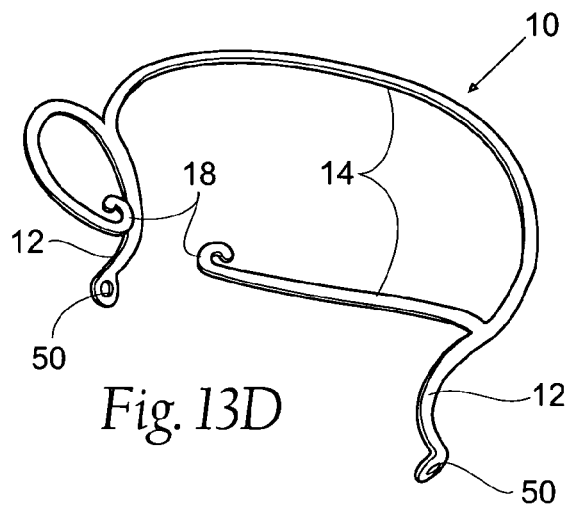
FIGS. 13D and 13E are side perspective views of illustrative embodiments of an elastic implant sized and configured to rest within or near the leaflet commissures of a dysfunctional heart valve annulus to reshape the annulus and restore leaflet coaptation, the implant defining an open annular structure that can be optionally closed.
Figure 13E:
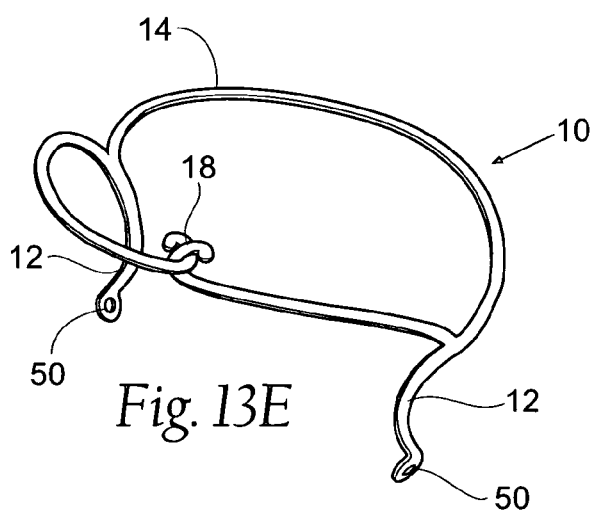

In FIG. 13A, the open annular shape is configured so that, when implanted, the implant 10 hugs the annulus. In FIG. 13B, the open annular shape is configured so that, when implanted, the implant rides above the annulus. FIGS. 13C and 13D show another style of open annular implant, one that hugs the annulus (FIG. 13C) and the other that rides above the annulus (FIG. 13D). In this arrangement, the interrupted rail 14 includes interlocking hooks 18 that can be coupled, if desired, to close the annulus of the implant 10 (see FIG. 13E). In FIG. 13E, the interlocked implant 10 is configured to ride above the annulus.

As FIGS. 13A and 13B show, the struts 12 need not be placed at diametrically opposite sides of the rail or rails 14. The commissures of a given valve annulus may not be at geometrically opposite sides of the annulus. Accordingly, the position of the struts 12 may be selected to conform to an asymmetric morphology of the annulus. The struts 12 may be used to simply locate the implant 10 in the valve, imparting little or no force on their own. In this arrangement, the annulus reshaping forces emanate from the rail or rails 14 above the commissures.

Figure 14:
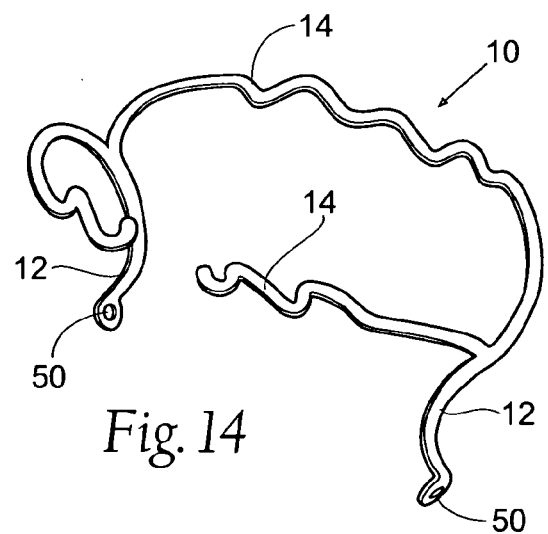
FIG. 14 is a side perspective view of an elastic implant of the open annular type shown in FIGS. 13D and 13E, showing how the mechanical characteristics of the implant can be varied along its structure, surface area, and interface with the tissue.

The implant possesses a spring constant that approximates the spring constant of tissue, making the implant more accommodating to the movement of the tissue. As FIG. 14 shows, a given rail or rails 14 can include undulations or the like to impart regions having different spring constants and/or mechanical properties along the length of the rail 14. Alternatively, or in combination, the cross-sectional width and/or thickness and/or geometry of a given rail 14 need not be uniform, but can vary along the length of the rail 14 to impart regions of different spring constants and/or mechanical properties. For example, in FIG. 13A, the region of the continuous rail 14 between the asymmetrically placed struts 12 may be thickened or thinned to impart different mechanical properties to achieve the desired shape changing objectives.

(ii) Foldable Elastic Annular Implants

Figure 15A:
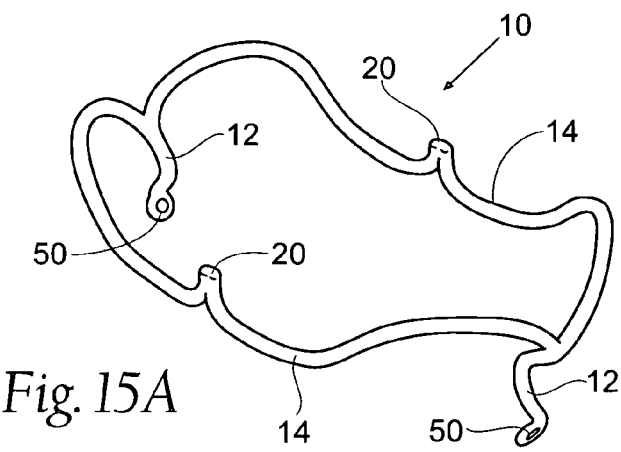
FIG. 15A is a side perspective view of another embodiment of an elastic implant sized and configured to rest within or near the leaflet commissures of a dysfunctional heart valve annulus to reshape the annulus and restore leaflet coaptation, the implant defining a closed annular structure that can be symmetrically folded upon itself.
Figure 15B:
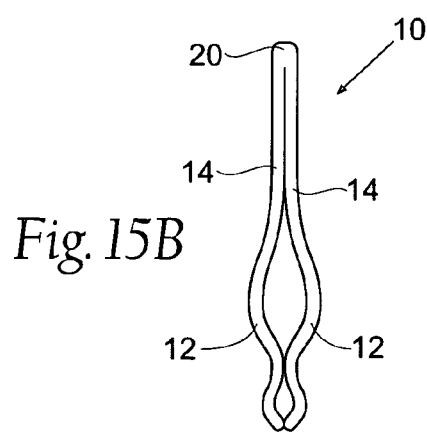
FIG. 15B is a side view of the implant shown in FIG. 15A when folded upon itself.
Figure 15C:
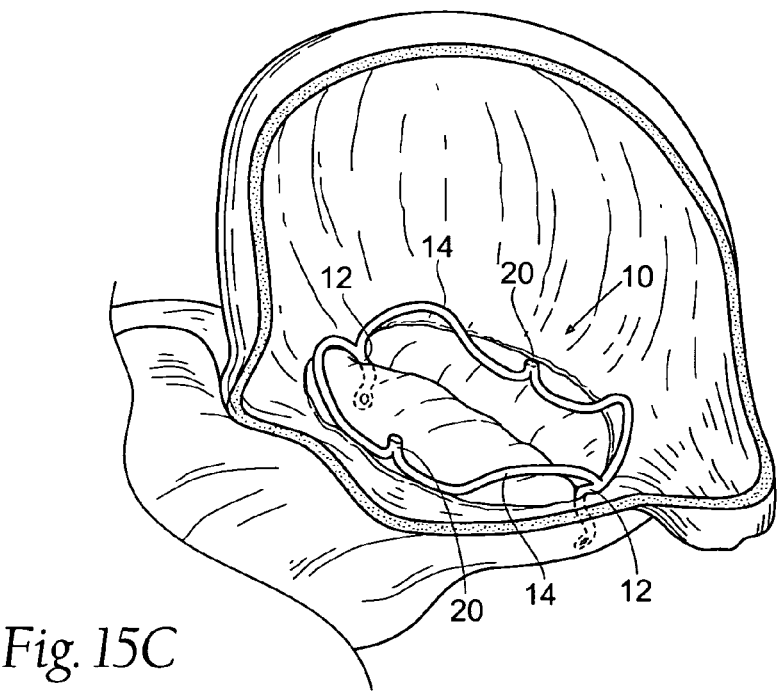
FIG. 15C is a perspective anatomic view, taken from an anterior and slightly superior viewpoint, of a mitral valve in which the elastic implant of the type shown in FIG. 15A has been implanted, showing the implant stretching the commissures to restore leaflet coaptation, and also showing the implant as hugging the annulus.

The implants 10 shown in FIGS. 15A to 15E comprise more than a single rail 14, imparting a normally closed, annular shape to the implant. Unlike the normally closed, annular implant 10 shown in FIG. 10, the rails 14 of the implants 10 shown in FIGS. 15A to 15E include cusps 20. The cusps 20 permit the implants to be resiliently folded along their minor (transverse axis) axis—with the cusps 20 occupying the fold—without permanently deforming the implant (see FIG. 15B). As will be described in greater detail later, an implant 10 of this type can be conveyed to an implantation site, e.g., within a catheter or sheath, in a folded as well as collapsed condition, and then deployed to assume the normally closed, annular shape shown in FIG. 15A, as FIG. 15C shows. As before explained, the shape and configuration of the rails 14 can be varied so that, when deployed, the implant hugs the annulus or rides above the annulus.

Figure 15D:
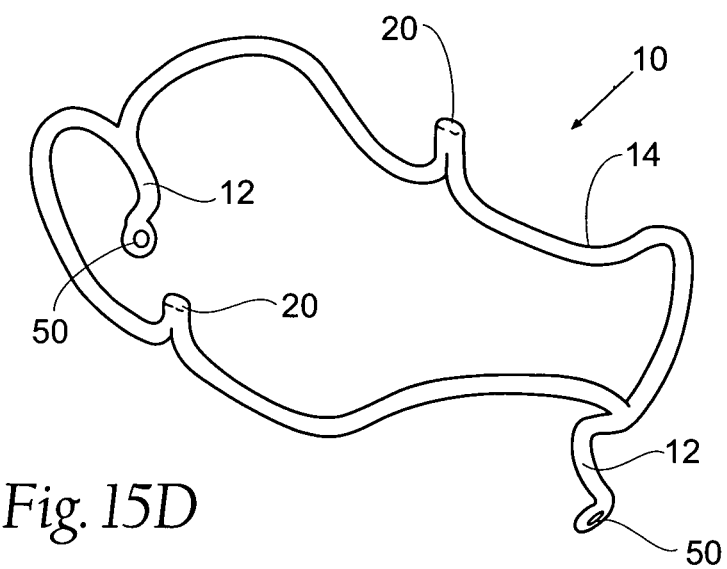
FIG. 15D is a side perspective view of another embodiment of an elastic implant sized and configured to rest within or near the leaflet commissures of a dysfunctional heart valve annulus to reshape the annulus and restore leaflet coaptation, the implant defining a closed annular structure that can be asymmetrically folded upon itself.
Figure 15E:
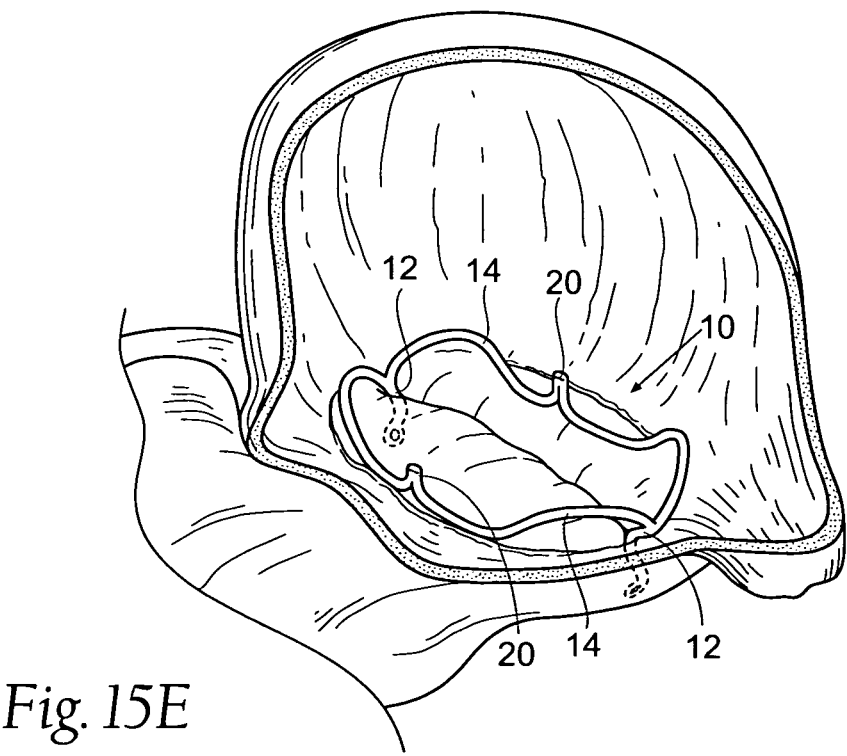
FIG. 15E is a perspective anatomic view, taken from an anterior and slightly superior viewpoint, of a mitral valve in which the elastic implant of the type shown in FIG. 15D has been implanted, showing the implant stretching the commissures to restore leaflet coaptation, and also showing the implant as hugging the annulus.

In FIG. 15A, the cusps 20 are symmetric, being formed on each rail 14 equidistant to the struts 12. In FIG. 15A, the struts 12 are also shown symmetric as to height above the rail 14. FIG. 15D shows that the cusps 20 need not be symmetric in either respect. As will be described in greater detail later, this asymmetry permits a stepwise, staggered deployment of the implant, in which the parts of the implant are deployed one at a time in succession—e.g., one strut, then one cusp, then another strut, and then the other cusp— until the implant assumes the closed, annular shape shown in FIG. 15D, as FIG. 15E shows.

(iii) Fixation of Implants

As before stated, the struts 12 can include other structures or mechanisms 16 to further enhance the anchorage and stabilization of the implant in the heart valve annulus. These structures or other mechanisms 16 can comprise, e.g., loops, pads, barbs, vertical legs, or circumferential legs, or other anchoring structures below, at, and/or above the valve plane. The structures and mechanisms 16 desirably increase the surface area of contact between the struts 12 and tissue adjoining the annulus. The structures and mechanism 16 desirably rely solely or partly on the valve and neighboring anatomic structures to anchor and fix the position of the implant in the annulus and resist its migration out of the annulus. Implant fixation can also assist in the achieving the desired coaptation of the leaflets and to resist upward movement or eversion of the leaflets during the cardiac cycle.

For example, in the embodiment shown in FIGS. 7A and 8, the rails 14 carry four struts 12, two supra-annular (contacting tissue on the atrial side of the valve) and two infra-annular (contacting tissue on the ventricular size of the valve). The struts 12 are separated by a thin spine that curves away from the struts 12 to avoid contact with the commissures themselves, so as not to interfere with the opening and closing of the valve.

As shown in FIG. 7A, the struts 12 may be cushioned to increase traction, decrease erosion, and improve their interaction with the valve annulus. In addition, the struts 12 may be coated, covered, or impregnated with a tissue growth promoting material. The rails 14 spanning the struts 12 functions to exert compressive forces on the annulus. The struts 12 are secured by the compression forces created by the rail's interaction with the valve annulus. The struts 12 assure that the implant is positioned correctly in situ, because they will only seat when positioned at or near the commissures of the valve.

The struts 12 may be sized and shaped in various ways. FIGS. 7B, 7C, and 7D show various embodiments with alternative designs for the struts 12. As another example, in FIG. 7E, the supra-annular struts 12 are somewhat larger than the infra-annular struts 12 to improve the anatomical fit of the device in situ.

Figure 16A:
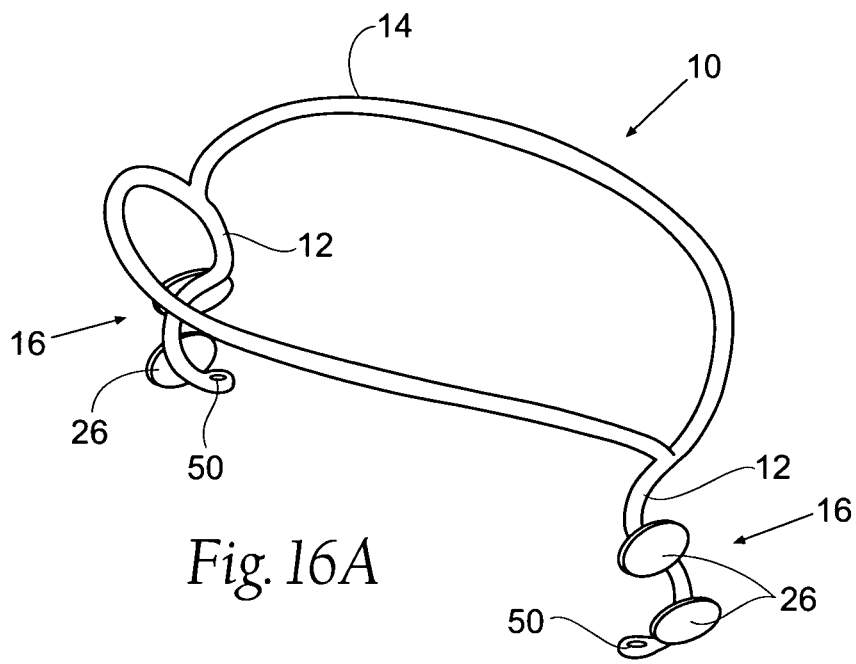
FIG. 16A is a side perspective view of an elastic implant of the type shown in FIG. 10, showing an illustrative embodiment of tab structures that serve to anchor and stabilize the implant in an annulus.
Figure 16B:
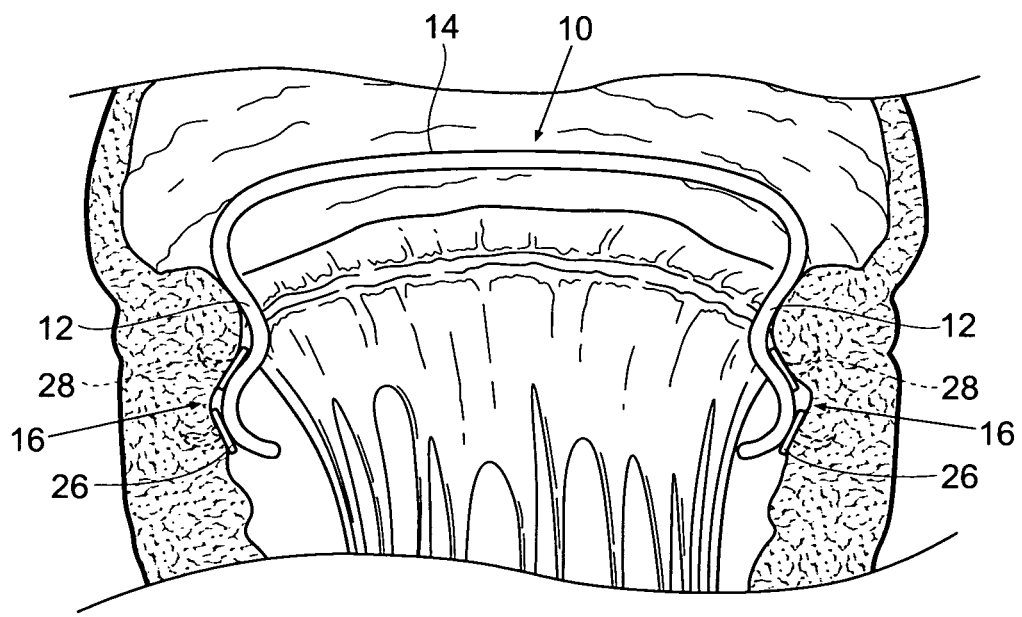
FIG. 16B is a side anterior anatomic view of a mitral valve annulus in which the elastic implant shown in FIG. 16A has been implanted.

In the embodiment shown in FIGS. 16A and 16B, the struts 12 can carry flat infra-annular tissue contacting pads 26, located below the plane of the valve annulus. The pads 26 rest on outwardly bowed extensions below the commissures, applying holding forces upon the heart walls. The pads 26 can take the form of flat surfaces, as FIGS. 16A and 16B show. Tissue penetrating barbs 28 (shown in phantom lines in FIG. 16B) may enhance the effect of the compression forces to fix the location of the implant.

Figure 17A:
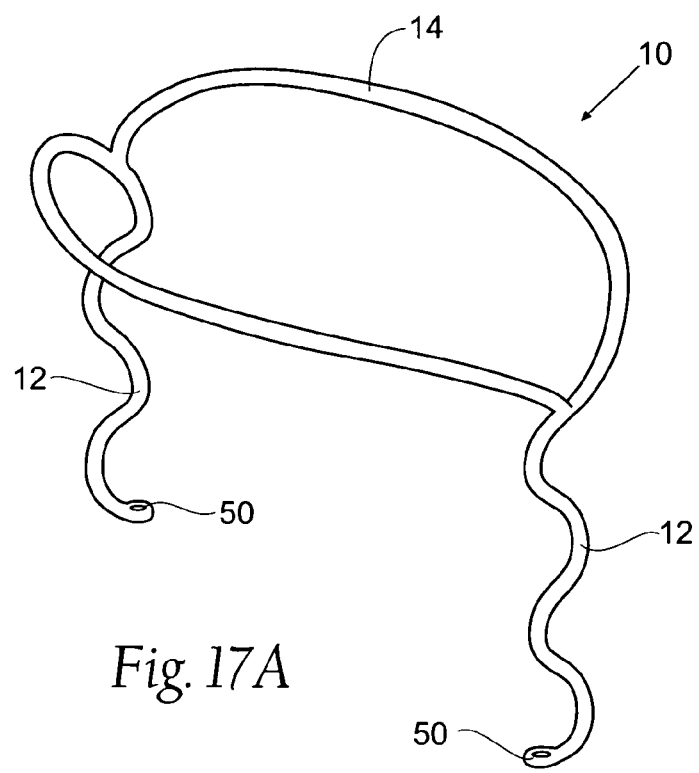
FIG. 17A is a side perspective view of an elastic implant of the type shown in FIG. 10, showing an illustrative embodiment of multiple contact structures that serve to anchor and stabilize the implant in an annulus.
Figure 17B:
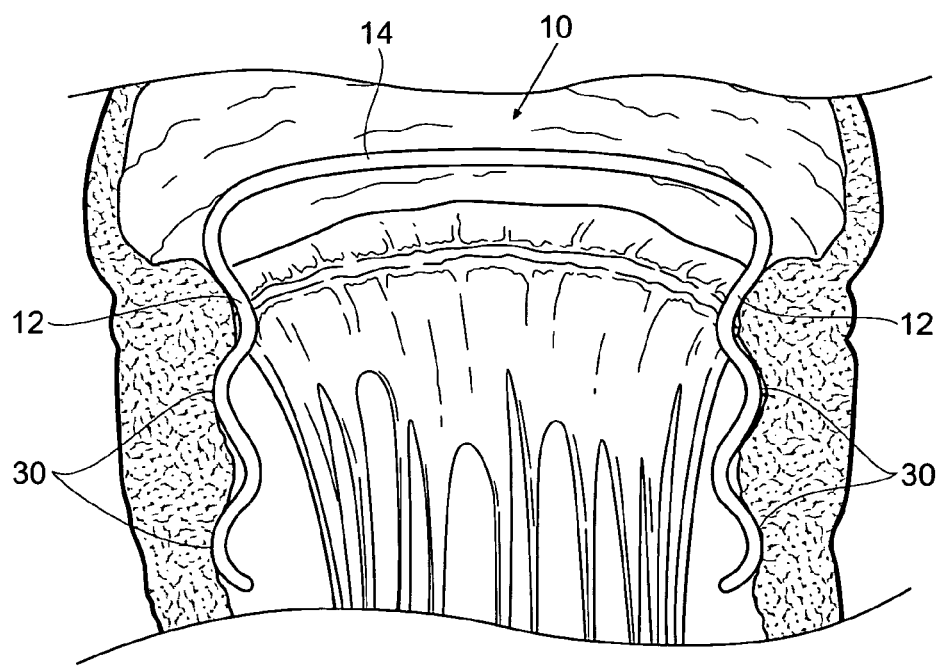
FIG. 17B is a side anterior anatomic view of a mitral valve annulus in which the elastic implant shown in FIG. 17A has been implanted.

As FIGS. 17A and 17B show, the struts 12 can extend in an undulating fashion below the plane of the valve annulus, to create a series of infra-annular contact surfaces 30 between the implant and the heart walls below and adjoining the annulus. The series of contact surfaces 30 increase the points of contact between the implant and tissue below the annulus. These multiple points of contact 30 are additive to the contact between the implant and tissue at or near the commissures themselves. In FIGS. 17A and 17B, additional struts and/or barbs or similar anchoring surfaces (such as shown in FIGS. 16A and 16B) are not shown associated with the contact surfaces, but they could be included, if desired.

Figure 18A:
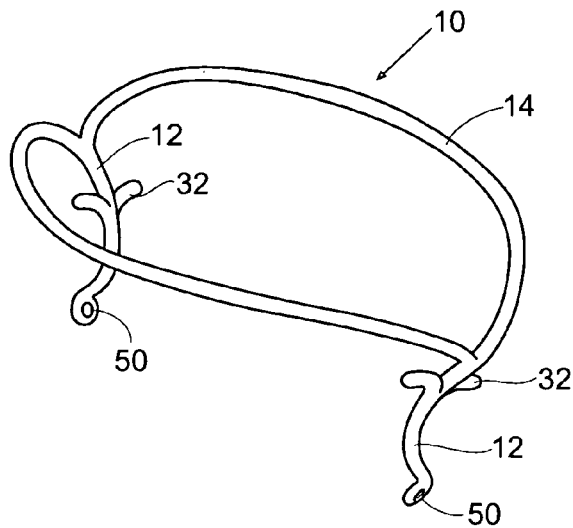
FIGS. 18A and 18B are side perspective views of an elastic implant of the type shown in FIG. 10, showing illustrative embodiments of frictional struts that serve to anchor and stabilize the implant in an annulus.
Figure 18B:
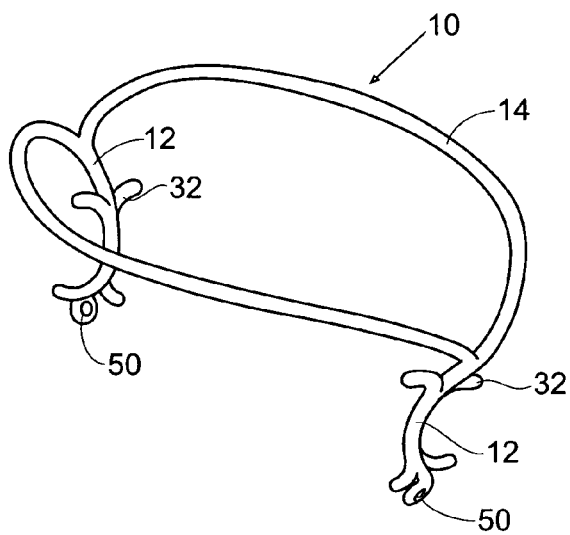

As FIGS. 18A and 18B show, the implant can include infra-annular frictional struts 32 located below the level of the annulus. The infra-annular frictional struts 32 engage tissue of the heart walls below and adjoining the annulus. The struts 32 resist migration of the implant out of the annulus. As FIG. 18A shows, the frictional struts 32 can be placed in a single level immediately below the commissures, or (as FIG. 18B shows) the struts 32 can be arranged in multiple levels below the commissures.

Figure 19:
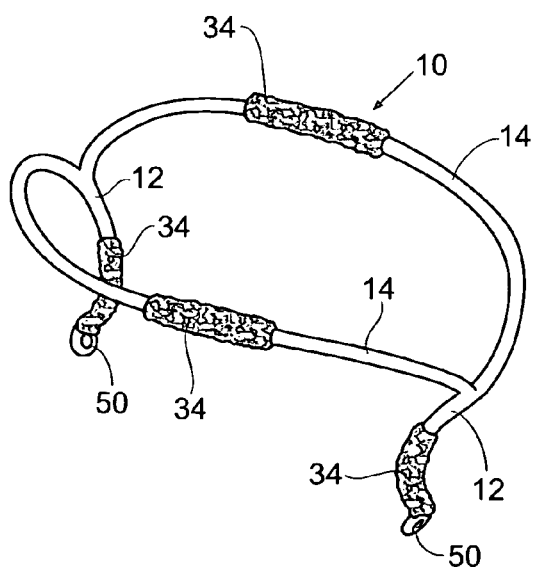
FIG. 19 is a side perspective view of an elastic implant of the type shown in FIG. 10, showing an illustrative embodiment of tissue in-growth surfaces that serve to anchor and stabilize the implant in an annulus.

As FIG. 19 shows, the struts 12 and/or the rails 14 can include tissue in-growth surfaces 34. The surfaces 14 provide an environment that encourages the in-growth of neighboring tissue on the implant. Once in-growth occurs, the implant 10 becomes resistant to migration or dislodgment from the annulus. Conventional in-growth materials such as polyester fabric can be used.

Any fixation mechanism or structure may, if desired, be combined with an adhesive or like material to further secure the implant.

II. Deployment of Elastic Implants for Reshaping a Heart Valve Annulus

The various implants as just described lend themselves to implantation in a heart valve annulus in various ways. They can be implanted, e.g., in an open heart surgical procedure. Alternatively, they can be implanted using catheter-based technology via a peripheral venous access site, such as in the femoral or jugular vein or femoral artery, or alternatively by thorascopically through the chest or by means of other surgical access through the right atrium.

A. Open Heart Surgical Procedures

Figure 21:
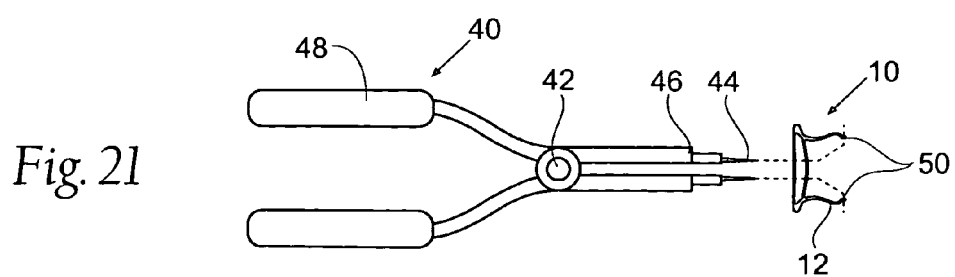
FIG. 21 is a side elevation view of a tool for implanting an elastic implant in a valve annulus in a open heart surgical procedure to reshape the annulus and restore leaflet coaptation.

FIG. 21 shows a tool 40 for deploying an elastic implant 10 of the type generally described in an annulus of a heart valve in an open surgical procedure. FIGS. 22A to 22F diagrammatically show the steps of an open surgical procedure for deploying the implant 10 in a mitral valve annulus using the tool 40 shown in FIG. 21.

The tool 40 includes a scissors-action mechanism 42 comprising an operating end 46 and a handle end 48. The operating end 46 includes prongs 44 that can be moved apart and together by manipulation of the handle end 48 (see FIGS. 22A and 22B). The prongs 44 are sized and configured to mate with deployment apertures 50 formed on the struts 12 of the implant 10 (shown in FIG. 21). The deployment apertures 50 are also shown in the implants in preceding FIGS. 10 to 19, which can be likewise be deployed using the tool 40.

In using the tool 40, the scissors-action mechanism 42 is manipulated to spread the prongs 44 apart (see FIGS. 22A and 22B), so that they can be mated in the apertures 50 of the implant 10. The scissors-action mechanism 44 is manipulated to bring the prongs 44 together, thereby applying force to the struts 12 to place the implant 10 in a compressed condition (see FIG. 22C).

With the tool 40 holding the implant 10 in this condition, the tool 40 and implant 10 are introduced through an open surgical approach into the left atrium. The tool 40 places the implant 10 within the mitral valve annulus (see FIG. 22D). As shown in FIG. 22D, the annulus is shown to have a dimension of D1. This dimension D1 is not conducive to leaflet coaptation, and regurgitation is occurring. It is the purpose of the surgical procedure to repair this dysfunction by reshaping the annulus with the implant 10.

The scissors-action mechanism 42 is manipulated to spread the prongs 44 apart until the struts 12 of the implant 10 rest within or near the commissures of the mitral valve (see FIG. 22E). At this point in the procedure, the dimension D1 of the annulus remains unchanged. The tool 40 is withdrawn, freeing the prongs 12 from the apertures 50 (see FIG. 22F). The elastic unloading of the implant 10 displaces and spreads the valve tissue apart, achieving a new dimension D2 for the annulus, which is larger than D1. The new dimension D2 is conducive to leaflet coaptation. The implant 10 has reshaped the annulus to restore valve function.

B. Illustrative Catheter-Based Intravascular Procedures
(i) Linear Deployment of Elastic Implants FIGS. 23 to 25 show a representative embodiment of a percutaneous catheter-based linear deployment of an unfolded elastic implant 10 of the type shown in FIGS. 7 to 14.

Figure 23A:
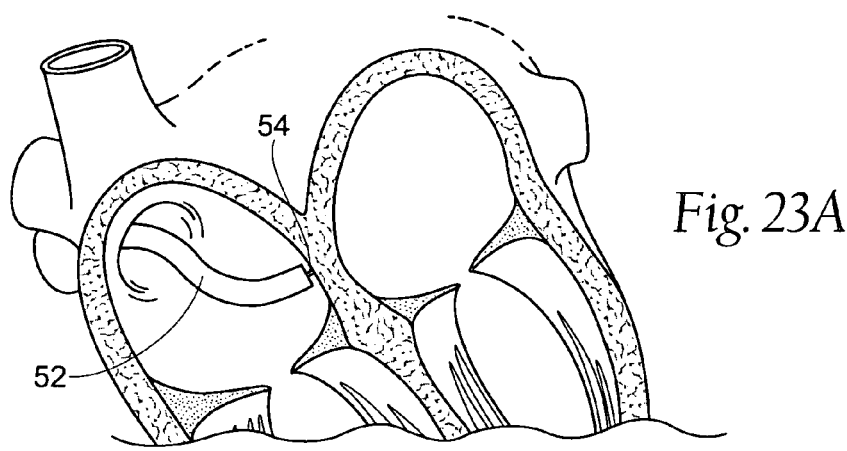
FIGS. 23A to 23C diagrammatically show a method of gaining intravascular access to the left atrium for the purpose of deploying a delivery catheter to place an implant in a valve annulus to reshape the annulus and restore leaflet coaptation.
Figure 23B:
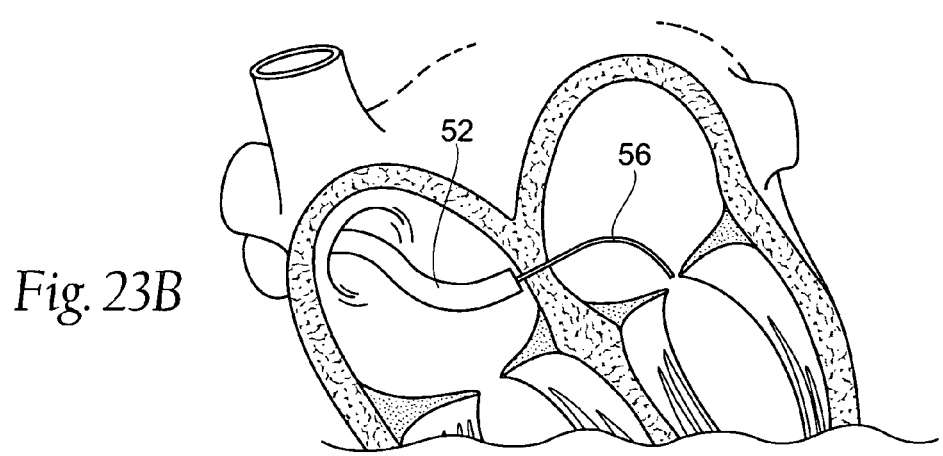
Figure 23C:
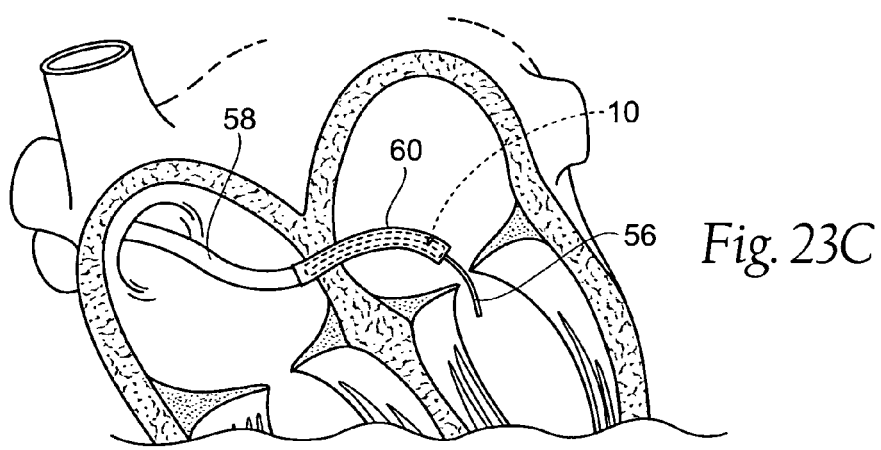

Percutaneous vascular access is achieved by conventional methods into the femoral or jugular vein. As FIG. 23A shows, under image guidance, a catheter 52 is steered through the vasculature into the right atrium. A needle cannula 54 carried on the distal end of the catheter is deployed to pierce the septum between the right and left atrium. As FIG. 23B shows, a guidewire 56 is advanced trans-septally through the needle catheter 52 into the left atrium. The first catheter 52 is withdrawn, and (as FIG. 23C shows) under image guidance, an implant delivery catheter 58 is advanced over the guidewire 56 into the left atrium into proximity with the mitral valve. Alternatively, the implant delivery catheter 58 can be deployed trans-septally by means of surgical access through the right atrium.

Figure 24:
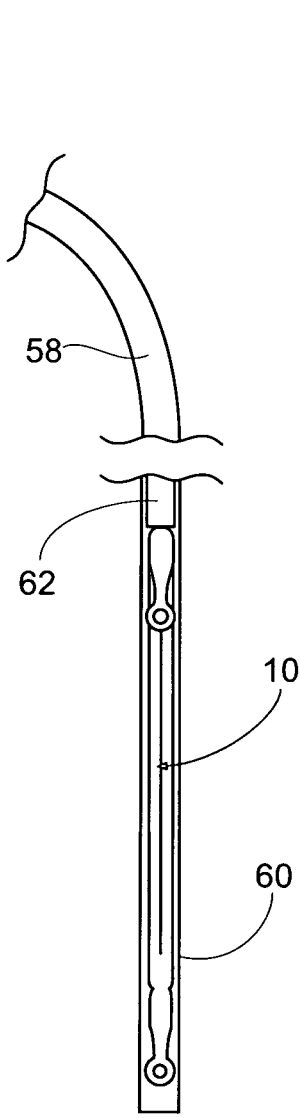
FIG. 24 is a side elevation view of the distal end of the implant delivery catheter shown in FIG. 23C, showing an elastic implant of the type shown in FIG. 10 collapsed in a sleeve for deployment into the left atrium in the manner shown in FIGS. 23A to 23C.

The implant delivery catheter 58 carries a sheath 60 at its distal end (see FIG. 24). The sheath 60 encloses an elastic implant 10 of a type shown in FIGS. 7 to 14. The implant 10 is constrained in a collapsed, straightened condition within the sheath, as FIG. 24 shows. The sheath 60 can be sized and configured to be withdrawn (e.g., by sliding it proximally), to free the implant 10. Free of the sheath 60, the elastic implant 10 will expand. Alternatively, a flexible push rod 62 in the catheter 58 can be used to expel the implant 10 from the sheath 60, with the same result. Desirably, the strut 12 on the trailing end of the implant 10 is folded within the sheath 60 to reduce the collapsed profile and facilitate the expansion of the implant 10 once free from the sheath 60.

Figure 25A:
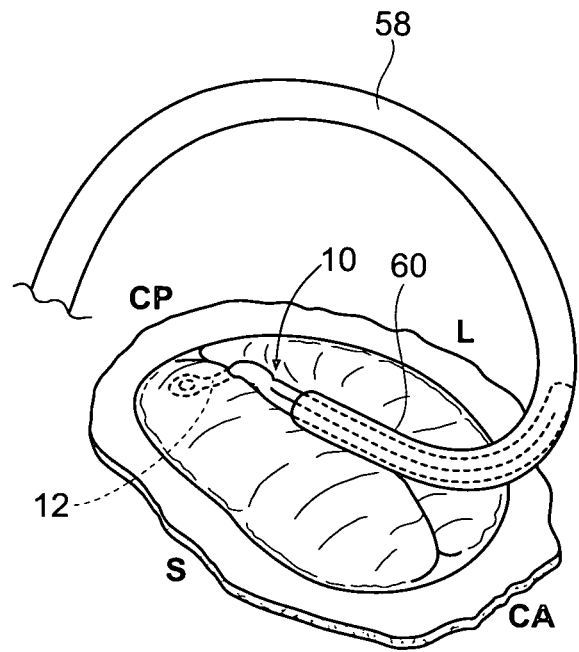
FIGS. 25A to 25E are diagrammatic perspective views of a method for manipulating the distal end of the implant delivery catheter shown in FIG. 24 to deploy an elastic implant of the type shown in FIG. 10 into a valve annulus to reshape the annulus and restore leaflet coaptation.
Figure 25B:
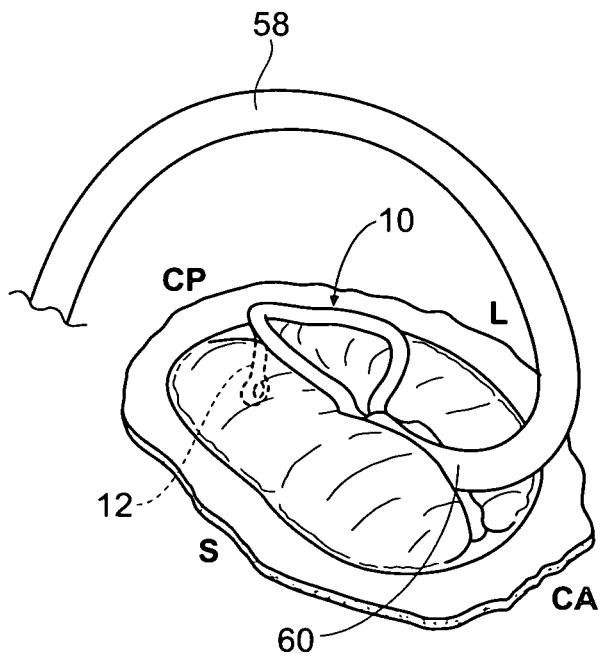
Figure 25C:
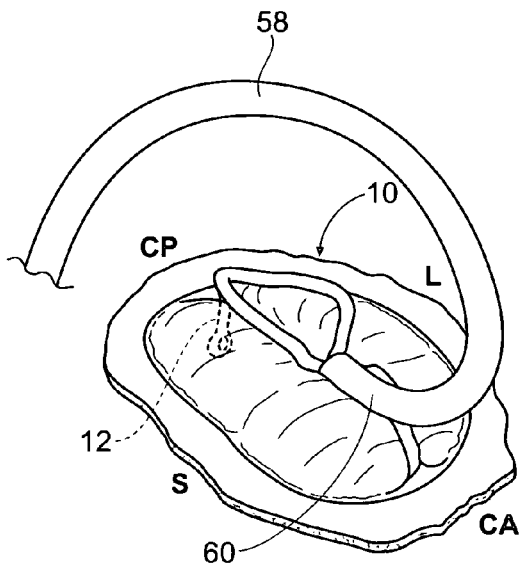
Figure 25D:
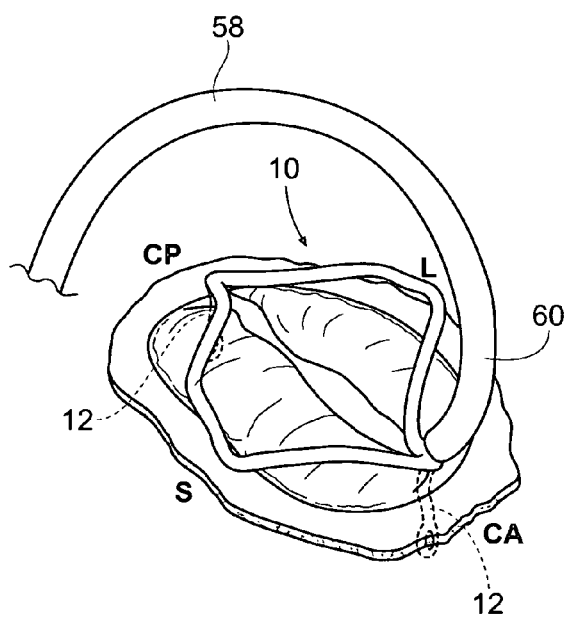

As FIG. 25A shows, under image guidance, the strut 12 on the leading end of the implant 10 is freed from the sheath 60 and seated retrograde in the posterior commissure of the valve annulus. Anchoring structures or mechanisms associated with the strut are also placed into desired contact with adjoining tissue below and/or above the plane of the annulus. As FIG. 25B shows, the delivery catheter 58 maintains force on the leading strut 12 within the posterior commissure, as the sheath 60 is withdrawn in line with the coaptation line in a posterior-to-anterior direction along the coaptation line. As shown in FIG. 25B, the delivery catheter 58 may need to dip down retrograde below the plane of the leaflets to maintain sufficient force on the leading end of the implant while the trailing end is freed from the sheath 60. However, as shown in FIG. 25C, the delivery catheter 58 may be sized and configured to have the column strength sufficient to maintain force on the leading strut without passage below the leaflet plane.

Figure 25E:
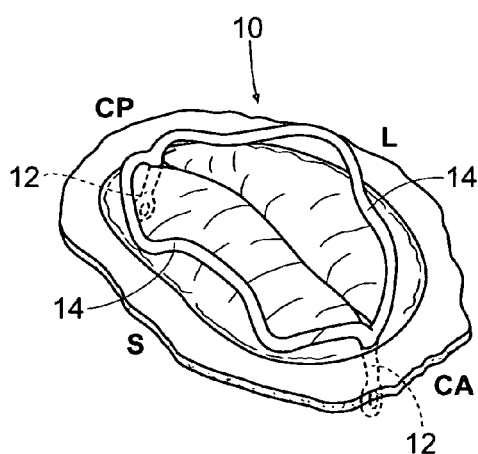

Progressively freed from the sheath 60, the elastic implant 10 shapes and seats (as FIGS. 25B/C and 25D shows), until the trailing strut 12 unfolds and seats within the anterior commissure (see FIG. 25E). The implant can also be positioned or repositioned under image guidance within the left atrium using a catheter-deployed grasping instrument.

(ii) Guide Loop Deployment of Unfolded Elastic Implants

FIGS. 26 and 27A to 27I show another embodiment of an implant delivery catheter 58 that can be used to deploy a folded elastic implant 10 of the type shown in FIGS. 7 to 14 within the left atrium.

Figure 26A:
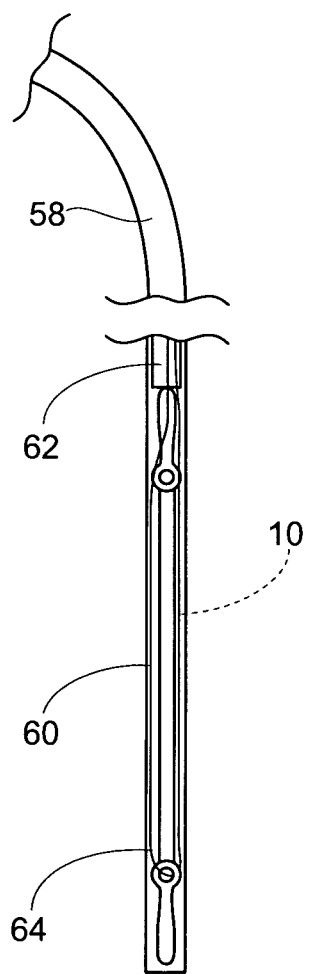
FIG. 26A is a side view of the distal end of the implant delivery catheter of the type shown in FIG. 23C, showing an elastic implant of the type shown in FIG. 10 collapsed in a sleeve for deployment into the left atrium in the manner shown in FIGS. 23A to 23C, also and showing the presence of a guide wire loop to aid in the deployment.

In this embodiment, as in the previous embodiment, the implant delivery catheter 58 includes a sheath 60 that constrains the implant 10 in a collapsed, straightened condition for passage into the left atrium (see FIG. 26). The sheath 60 is sized and configured to be withdrawn (e.g., by sliding it proximally), to free the implant for expansion within the left atrium, or a push rod 62 can be used to eject the implant from the sheath 60. To create a desired profile, one or both struts can be folded against the body of the implant within the sheath 60.

Unlike the previous embodiment, a metallic, fiber, or polymer guide wire 64 is looped through the deployment apertures 50 on the struts 12 of the implant 10 prior to the insertion of the implant 12 into the sheath 60. The legs of the resulting guide wire loop 66 are passed out the proximal end of the sheath 60 for manipulation, as will now be described.

In use, the implant delivery catheter 58 is introduced trans-septally into the left atrium in the manner previously described. With the distal end of the catheter 58 positioned above the valve annulus (see FIG. 27A), and prior to withdrawal of the sheath 60, both legs of the guide wire loop 66 are advanced distally in tandem through the sheath 60 to advance the loop 60 beyond the deployment apertures 50 and out the distal end of the sheath 60. The guide wire loop 66 desirably carries radio-opaque markers 68 to aid in fluoroscopic visualization. The markers 68 identify a desired distance between them and the distal end of the sheath 60, marking a space in which the implant 10 can freely expand without contacting tissue or anatomic structures within the atrium. Guided by the markers 68, the loop 66 can be dropped into the annulus a desired distance beyond the distal end of the sheath 60, as FIG. 27A shows.

With the loop 66 positioned in the desired way within the annulus, the sheath 60 can be withdrawn to free the implant 10 for expansion (see FIG. 27B). While tethered to the guide wire loop 66, the implant 10 opens within the left atrium—first one strut, then the other—as the sheath 60 is withdrawn, as FIGS. 27C and 27D show.

Once the implant 10 is fully free of the sheath 60 and expanded, both legs of the guide wire loop 66 can be advanced proximally in tandem through the sheath 60 (see FIG. 27E). The wire loop 66 applies force to the struts 12 and brings them together (see FIG. 27F). This places the implant 10 in a compressed, elastically loaded condition. Proximal advancement of the legs of the wire loop 66 also draws the implant 10 in this condition snuggly against the distal end of the catheter 58 for greater control, as FIG. 27F shows.

With the implant 10 tethered to the catheter 58 in this condition (see FIG. 27G), the catheter 58 can be advanced under image guidance to place the implant 10 within the annulus. Manipulation of the catheter 58 will bring the struts of the implant into desired alignment. Subsequent distal advancement of the legs of the wire loop 66 (see FIG. 27H) allows the struts of the implant 10 to be elastically unloaded and brought into contact with the surrounding tissue. Anchoring structures or mechanisms associated with the struts 12 can also be placed into desired contact with adjoining tissue below and/or above the plane of the annulus. The legs of the wire loop 66 can be manipulated to pull the struts 12 together and/or allow them to separate, until the desired orientation and tissue contact in and about the annulus are achieved.

Once desired orientation and tissue contact are achieved for the implant 10, one leg of the wire loop 66 can be pulled to release the implant from the guide wire 64 (see FIG. 27I). The implant 10 is allowed to fully unfold and seat within the annulus.

Figure 28B:
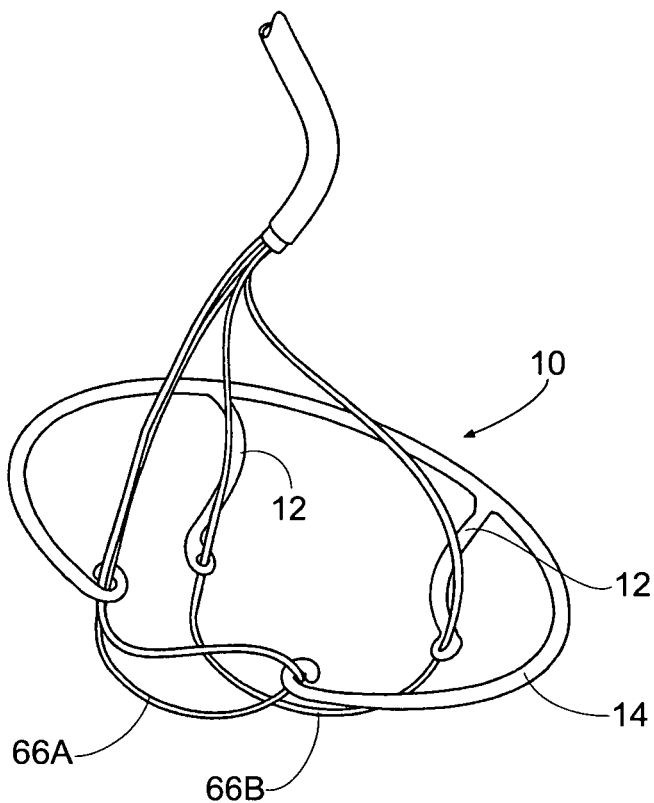
FIGS. 28A and 28B are perspective view of elastic implants of the type shown in FIGS. 13B to 13E, showing the tethering of such implants to one or more wire loops to aid in their deployment into a valve annulus to reshape the annulus and restore leaflet coaptation.
Figure 28A:
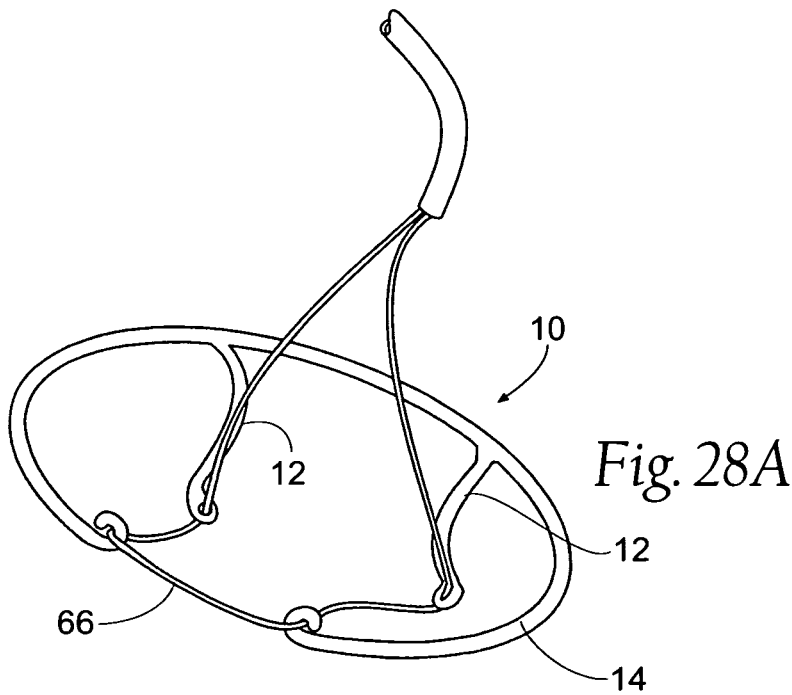

A guide loop 66 can be used to deploy open annular implants as well as closed annular implants. As shown in FIG. 28A, a single guide loop 66 can be threaded through an open annular implant 10 of the type shown in FIG. 13B. Or, as shown in FIG. 28B, two guide wire loops 66A and 66B can be threaded through an inter-locking implant of the type shown in FIGS. 13D and 13E. In this arrangement, the first guide wire loop 66A can be manipulated to position the struts 12 of the implant within the annulus, as just described. The second guide wire loop 66B can be separately manipulated to pull the rails 14 together for interlocking, once the struts rest in a desired manner in the commissures.

(iii) Deployment of Folded Elastic Implants

FIGS. 15A to 15E show elastic implants 10 that can be folded about cusps 20. As FIG. 29 shows, the folding allows the implant 10 to be conveyed into the left atrium within a sheath 60 of an implant delivery catheter 58 with a delivery profile that not only constitutes a side-to-side collapsed condition—which minimizes the delivery profile diameter—but also constitutes a lengthwise folded condition—which minimizes the delivery profile length.

FIGS. 30A to 30D illustrate the deployment of a symmetrically folded elastic implant 10 of the type shown in FIGS. 15A and 15B. The implant 10 is constrained in a symmetrically folded and collapsed condition within the sheath 60, as FIG. 30A shows. In this condition, the struts 12 form the leading end of the implant. A push rod 62 in the catheter 58 includes a gripping mechanism 70 that holds the folded implant 10 by the cusps 20. The push rod 62 is advanced to expel the implant 12 from the sheath 60, both struts 12 first.

As FIG. 30B shows, under image guidance, the folded implant 10 is aligned with coaptation line generally equidistant from the commissures, with the struts 12 oriented to face the commissures (the delivery catheter 58 has been previously introduced trans-septally into the left atrium, as already described). Manipulating the push rod 62 advances the implant 10, both struts first, from the sheath 60. Connecting the push rod 62 to the implant 10 allows the implant 10 to be translated and rotated and retracted during deployment. Freed from the sheath 60 (see FIG. 30B), the implant 10 begins to unfold along the cusps 20, and the struts 12 draw apart toward the commissures. Further advancement of the push rod 62 frees more of the unfolding implant 10 from the sheath 60, until the struts 12 draw apart sufficiently to contact the commissures (as FIG. 30C shows). Prior to release of the cusps 20 from the gripping mechanism 70, the implant 10 can be manipulated to assure that anchoring structures or mechanisms associated with the strut are placed into desired contact with adjoining tissue below and/or above the plane of the annulus. The gripping mechanism 70 can then be activated (see FIG. 30D), releasing the implant 10.

FIGS. 31A to 31E illustrate the deployment of an asymmetrically folded elastic implant 10 of the type shown in FIGS. 15D and 15E. The implant 10 is constrained in an asymmetrically folded and collapsed condition within the sheath 60, as FIG. 31A shows. The gripping mechanism 70 holds one, but not both of the cusps 20. This is because the height of the cusps 20 above the rails 14 is also asymmetric. The gripping mechanism 70 will couple to the taller cusp 20. The push rod 62 can be advanced to expel the implant 10 from the sheath 60. Due to the asymmetry of the cusps 20, one of the struts 12 is positioned for deployment before the other strut 12. Also due to the asymmetry of the cusps 20, the shorter cusp 20 is positioned for advancement out of the sheath 60 before the taller cusp 20 is released by the gripping mechanism 70.

As FIG. 31B shows, under image guidance, the folded and collapsed implant 10 is aligned with coaptation line near one of the commissures (the delivery catheter 58 has been previously introduced trans-septally into the left atrium, as already described). Manipulating the push rod 62 advances the implant 10 from the sheath 60. The leading strut 12 is freed first (see FIG. 31B) and placed against the adjacent commissure. The implant 10 can be manipulated to assure that anchoring structures or mechanisms associated with the leading strut are placed into desired contact with adjoining tissue below and/or above the plane of the annulus. Further advancement of push rod 62 causes the implant 10 to unfold toward the opposite commissure. Continued advancement of the push rod 62 frees more of the unfolding implant 10 from the sheath 60, until the trailing strut 12 contacts the opposite commissure (as FIG. 31C shows). The implant 10 can be manipulated to assure that anchoring structures or mechanisms associated with the trailing strut 12 are placed into desired contact with adjoining tissue below and/or above the plane of the annulus. Further advancement of the push rod 62 frees the shorter cusp 12 from the sheath 60, and the implant 10 springs open along this side (see FIG. 31D). The gripping mechanism 70 can then be activated (see FIG. 31), releasing the taller cusp 12. The implant 10 springs open in this direction. It can be seen that the asymmetry of the implant 10 make possible a step-wise deployment of the implant 10, one component at a time, in the annulus.

(iv) Guide Wire Assisted Deployment of Folded Elastic Implants

The use of one or more guide loops 66 or tethers to assist in the deployment of unfolded elastic implants has been previously discussed. One or more guide loops 66 or tethers can likewise be employed to assist in the deployment of folded elastic implants of either symmetric or asymmetric types.

For example, as shown in FIG. 32, a metallic, fiber, or polymer guide wire 64 can be looped through the deployment apertures on the struts of a folded symmetric or asymmetric implant 10 prior to the folding and insertion of the implant 10 into the sheath 60. The legs of the resulting guide wire loop 66 are passed out the proximal end of the sheath 60 for manipulation.

In use (see FIG. 33A)—after the implant delivery catheter 58 is introduced trans-septally into the left atrium in the manner previously described, and prior to activation of the push rod 62—both legs of the guide wire loop 66 are advanced distally in tandem through the sheath 60 to advance the loop 66 beyond the deployment apertures and out the distal end of the sheath 60. The loop 66 is placed within the annulus.

The push rod 62 is manipulated to free the folded implant 10 for expansion (see FIG. 33B). The implant 10 opens while tethered to the guide wire loop 66. The loop 66 increases in diameter as the struts 12 expand apart. The perimeter of the loop 66 will orient itself along the greatest dimension of the annulus—which is the distance between the commissures. The loop 66 thereby orients the implant 10 with the coaptation line during implant 10 expansion. The legs of the loop 66 guide the struts 12 to the commissures (as FIG. 33C shows).

Tethered to the catheter 58, the implant 10 is deployed in the annulus. The guide wire loop 66 maintains control of the strut spacing within the commissures during implant expansion.

Once desired orientation and tissue contact are achieved for the implant 10, the gripping mechanism 70 can release the implant 10. One leg of the wire loop 66 can be pulled to release the implant 10 from the guide wire (see FIG. 33D). The implant 10 is allowed to fully unfold and seat within the annulus.

Figure 34:
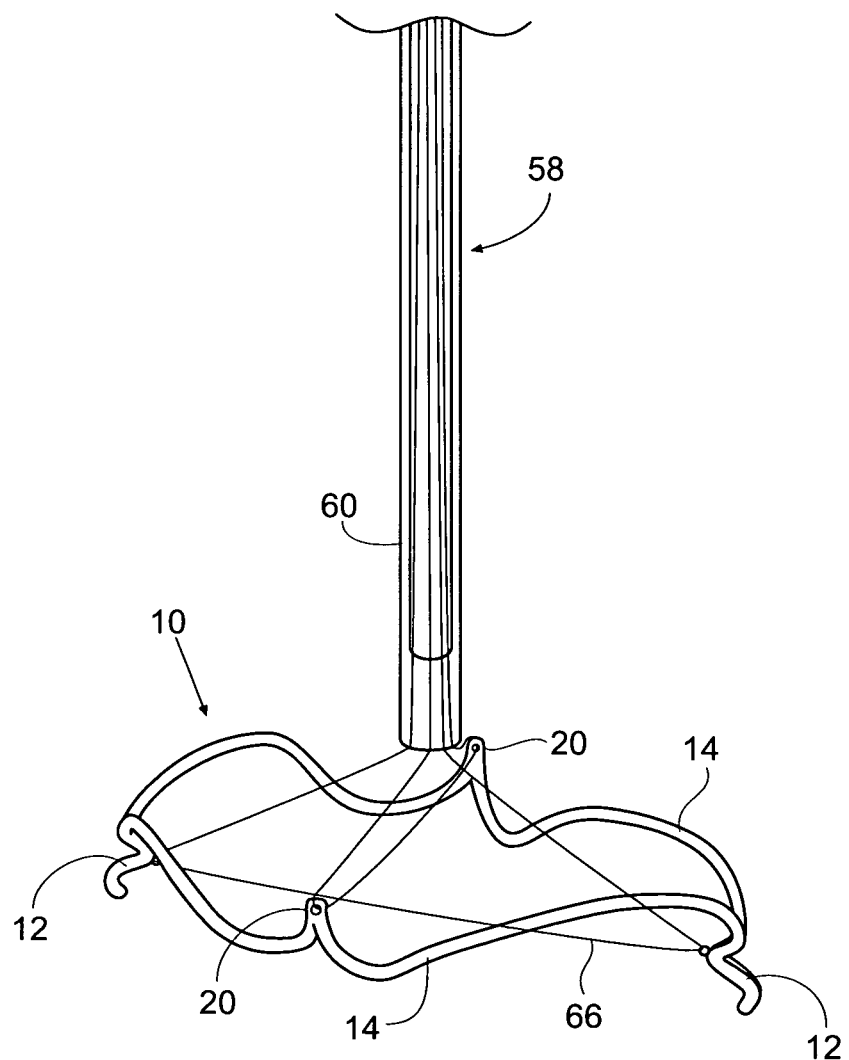
FIG. 34 is a side elevation view of the distal end of the implant delivery catheter of the type shown in FIG. 23C, showing a symmetrical foldable elastic implant of the type shown in FIG. 15A tethered to two guide wire loops to aid in its implantation into a valve annulus to reshape the annulus and restore leaflet coaptation.

As FIG. 34 shows, a second guide wire loop 72 can also be passed through apertures on the cusps 20. This guide wire loop 72 can be manipulated independently of the first guide wire loop 66, to control deployment of the expanding implant 10 in the septal-to-lateral dimension. Simultaneous, although independent, control of the expanding implant 10 can be achieved by manipulation of the first guide wire 66.

As FIGS. 35 and 36A to 36D show, separate metallic, fiber, or polymer guide wires 92 can be individually threaded (without looping) through the deployment apertures on the struts of a folded symmetric or asymmetric implant 10 prior to the folding and insertion of the implant 10 into the sheath 60 (see FIG. 35). The separate guide wires 92 are passed out the proximal end of the sheath 60 for manipulation.

In use (see FIG. 36A)—after the implant delivery catheter 58 is introduced trans-septally into the left atrium in the manner previously described, and prior to activation of the push rod 62—the separate guide wires 92 are advanced distally in tandem through the sheath 60 and out the distal end of the sheath 60. The ends of the wires 92 are placed within the annulus.

The push rod 62 is manipulated to free the folded implant 10 for expansion (see FIG. 36B). The implant 10 opens while tethered to the separate guide wires 92. The guide wires 92 will orient themselves along the major axis of the annulus—which is the distance between the commissures, to orient the implant 10 with the coaptation line during implant 10 expansion. The guide wires 92 separately guide the respective struts 12 to the commissures (as FIG. 36C shows).

Tethered to the catheter 58, the implant 10 is deployed in the annulus. The guide wires 92 maintain control of the strut spacing within the commissures during implant expansion.

Once desired orientation and tissue contact are achieved for the implant 10, the gripping mechanism 70 can release the implant 10. The guide wires 92 can be pulled to release the implant 10 from the guide wires (see FIG. 36D). The implant 10 is allowed to fully unfold and seat within the annulus.

(v) Other Forms of Assisted Deployment of Folded Elastic Implants

The foregoing embodiments demonstrate that the unfolding of an elastic implant 10 can be controlled during deployment in either the major axis dimension, or the minor axis (septal-to-lateral) dimension, or in both dimensions by means of guide wires. Other forms of restraining mechanisms can be used to control the unfolding of the implant 10.

Figure 37A:
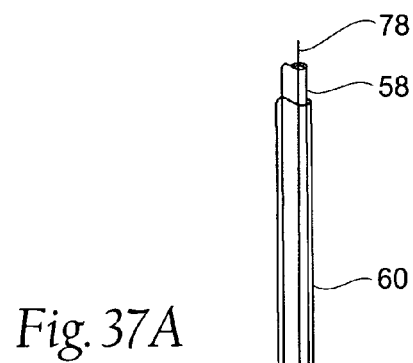
FIGS. 37A to 37C are diagrammatic views of the deployment a symmetrically folded and collapsed elastic implant of the type shown in FIG. 15A into a valve annulus with the aid of a wrapper or bag to reshape the annulus and restore leaflet coaptation.
Figure 37B:
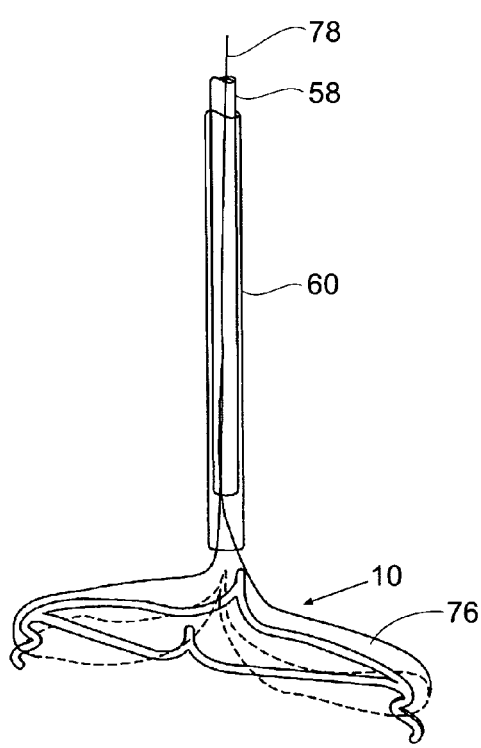
Figure 37C:
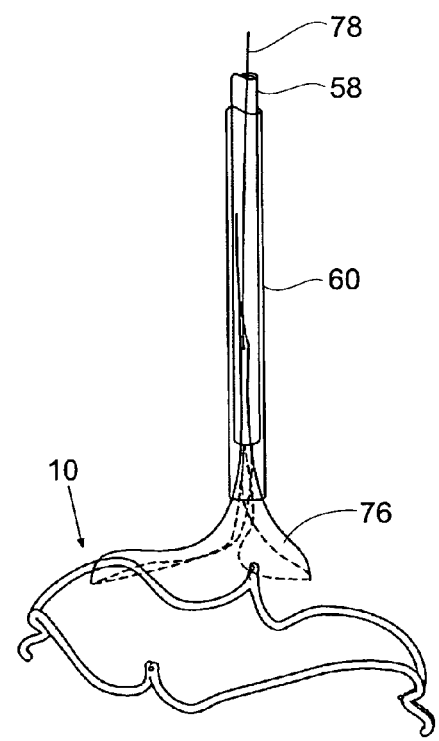

For example, as shown in FIG. 37A, the folded implant 10 can be restrained within a bag or wrapper 76 as the implant 10 is advanced from the delivery sheath 60. The bag or wrapper 76 restricts expansion of the implant 10 beyond a selected point (e.g., 80% of full deployment), allowing the physician to attend to the important task of seating the struts in the commissures before the implant 10 fully opens across the annulus. Once the implant 10 has been seated in the commissures and released from the delivery sheath 60 (see FIG. 37B), a ripcord 78 coupled to the bag or wrapper 76 can be pulled, to release the bag or wrapper 76 from the implant 10 (see FIG. 37C). Freed from the bag or wrapper 76, the implant 10 completes its expansion, to achieve final shaping and seating within the annulus. One or more guide wires can be used in combination with the bag or wrapper 76. The bag or wrapper 76 can alternatively be sized and configured to tear away as a result of the implant 10 expanding beyond a given point, without the use of a ripcord 78 or similar induced tearing mechanism. In another arrangement, the implant 10 can be enclosed within a shrink-wrap structure having a score line. In these arrangements, the structure is sized and configured to restrain expansion of the implant 10 until the implant 10 is advanced outside of the delivery sheath beyond a given point, at which time the score line parts or the material strength of the structure is exceeded, to open and fully release the implant 10.

Figure 38:
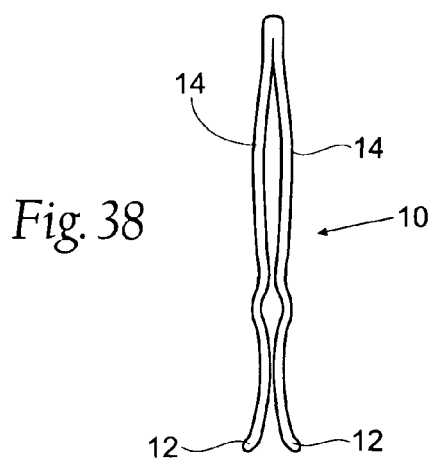
FIG. 38 is a side perspective view of a plastically deformable implant sized and configured to be expanded in situ to rest within or near the leaflet commissures of a dysfunctional heart valve annulus to reshape the annulus and restore leaflet coaptation.
Figures 39A, 39B, 39C:
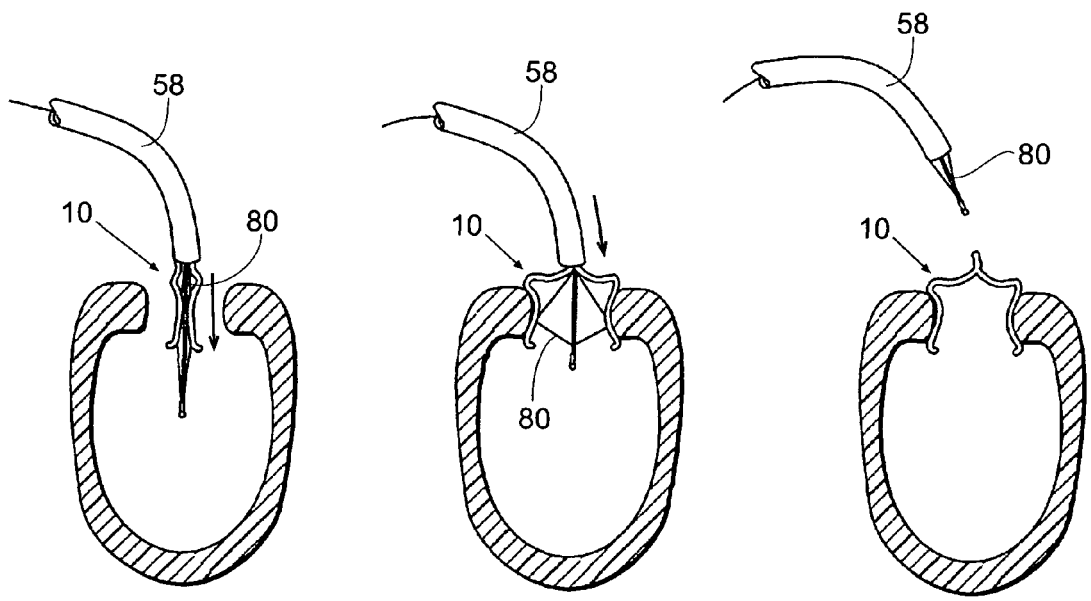
FIGS. 39A to 39C are diagrammatic views of the deployment of a plastically deformable implant of the type shown in FIG. 38 into a valve annulus with the aid of a mechanical expansion device.
Figure 40A:
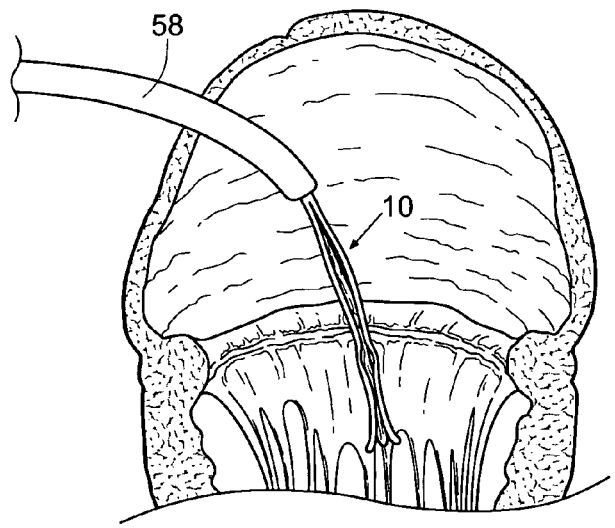
FIGS. 40A to 40C are diagrammatic anatomic views of the deployment of a plastically deformable implant of the type shown in FIG. 38 into a valve annulus with the aid of a balloon expansion device.
Figure 40B:
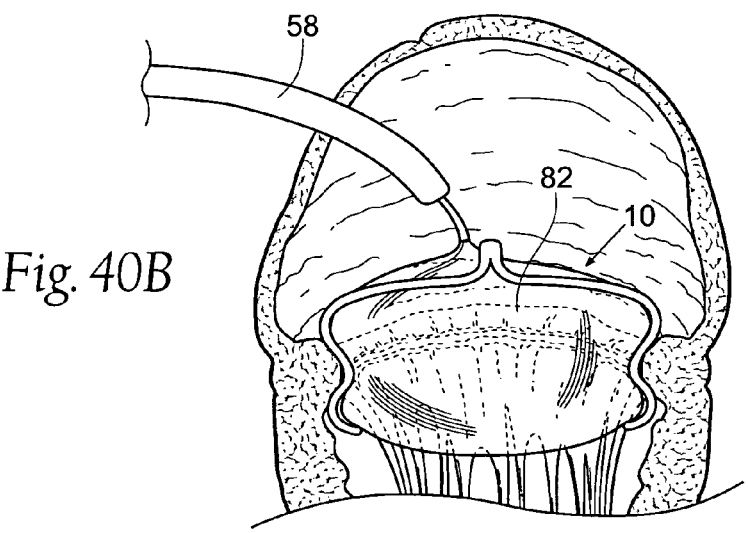
Figure 40C:
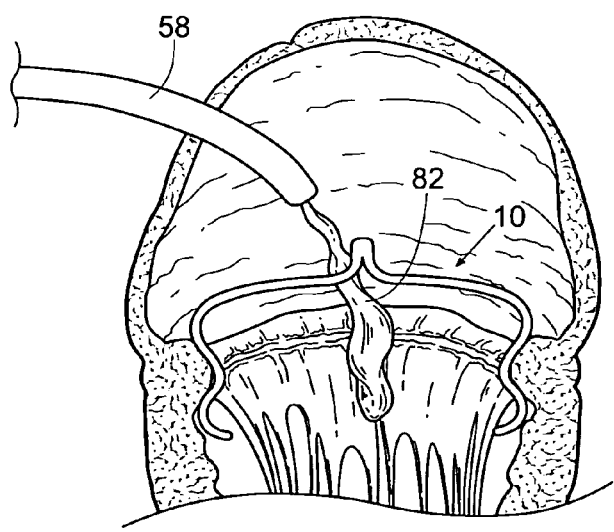

III. Plastically Deformable Implants for Reshaping Heart Valve Annulus and their Deployment As previously described, the implant 10 may be formed from plastically deformable material (see FIG. 38). The implant 10 includes struts and one or more rails, as previously described. The implant 10 is deployed by an implant delivery catheter 58 into the left atrium in a normally collapsed condition. In this arrangement, an implant delivery catheter 58 can carry a mechanical expansion device 80, such as a scissorjack or the like (see FIGS. 39A to 39C), to expand the plastically deformable material of the implant 10 in situ within the annulus. Alternatively, an implant delivery catheter 58 can carry an inflatable body 82 (e.g., balloon) (see FIGS. 40A to 40C), to expand the implant 10 within the annulus. During expansion, the plastically deformable implant 10 stretches the annulus to achieve a desired major axis size. Once expanded, the plastically deformable implant 10 maintains the desired distance, thereby resisting contraction of the annulus. The plastically deformable implant 10 may include other structures or mechanisms to further anchor and stabilize the implant 10 in the heart valve annulus.

IV. Ascertaining Implant Size and Resistance

The shape and structure of a heart valve such as a mitral valve and the neighboring anatomic structures are generally understood by medical professionals using textbooks of human anatomy along with their knowledge of the site and its disease or injury. Ranges of shapes and dimensions for a given implant are defined by the site to be treated. Precise dimensions for a given patient can be determined by X-ray, MRI, or CT scanning of the site to be treated prior to implantation of an implant.

Figure 41:
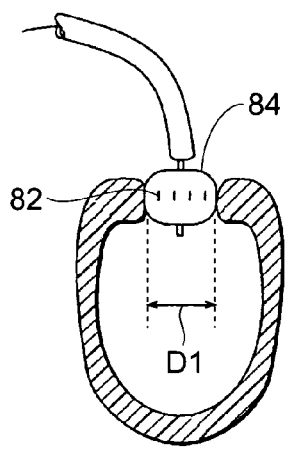
FIG. 41 is a diagrammatic view of a non-compliant balloon deployed into a valve annulus for the purpose of assessing the size and mechanical properties of an implant for the annulus.

A physician may also ascertain the size and resistance for a given implant by the deployment of a non-compliant balloon gauge 84 in the targeted annulus, as shown in FIG. 41. The balloon gauge 84 can carry radio-opaque markers 86 so that dimensions of the annulus can be determined using imaging means and/or other forms of in situ visualization. The compliance and tension forces of the annulus can also be physically measured, by sensing and quantifying the resistance the balloon gauge 84 encounters during expansion in the annulus. Based upon this data, and taking into account the physician's knowledge of the site and its disease or injury, a physician can select a desired size and mechanical properties for the implant.

V. Multi-Functional Implants

Various embodiments of implants 10 have described the context of reshaping a heart valve annulus. A given implant 10 having technical features suited for this function can also incorporate other technical features well suited for other functions.

Figure 42:
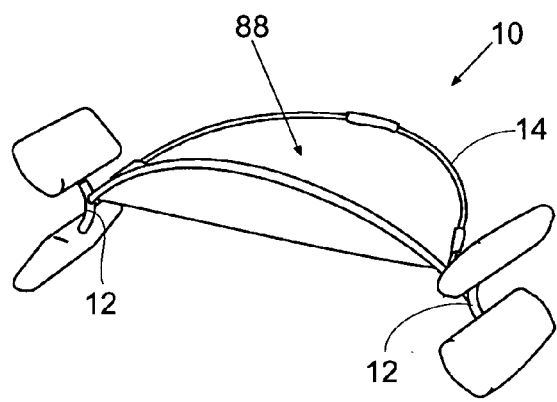
FIG. 42 is a side perspective view of a multi-functional elastic implant sized and configured to rest within or near the leaflet commissures of a dysfunctional heart valve annulus to reshape the annulus and restore leaflet coaptation as well serve as a neo-leaflet to either replace or supplement a damaged heart valve leaflet.

By way of illustration, FIG. 42 shows an annulus remodeling implant 10 in which the rails 14 are sized and configured to define a pseudo-annulus. A neoleaflet element 88 comprising a fabric-covered bridge structure is coupled to the rails. The neoleaflet element is sized and configured to occupy the space of at least a portion of a native heart valve leaflet to provide a one-way valve function. In response to diastolic pressure, the one-way valve function assumed a valve opened condition within the pseudo-annulus. In response to systolic pressure, the one-way valve function assumes a valve closed condition within the pseudo-annulus. The neoleaflet element 88 serves to either repair or replace or supplement a damaged heart valve.

Figure 43:
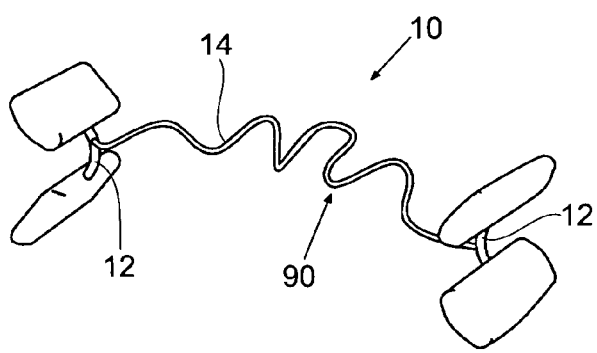
FIGS. 43 and 44 are side perspective views of a multi-functional elastic implants sized and configured to rest within or near the leaflet commissures of a dysfunctional heart valve annulus to reshape the annulus and restore leaflet coaptation as well serve as a leaflet retainer to prevent a native valve leaflet from being pushed into the atrium upon ventricular contraction.
Figure 44:
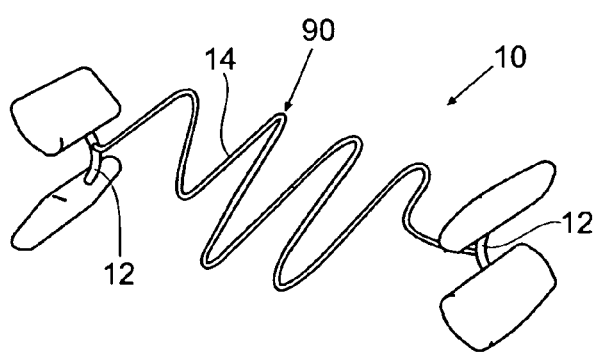

FIGS. 43 and 44 show an annulus remodeling implant 10 in which the rails 14 are sized and configured serve as a pseuedo-annulus. The implant 10 includes a retaining structure 90 near or within the pseudo-annulus that is sized and shaped to overlay at least a portion of one or more native valve leaflets. The retaining structure 90 retains a native valve leaflet during ventricular contraction, keeping the valve leaflet from being pushed into the atrium, i.e., eversion and/or prolapse.

Figure 45:
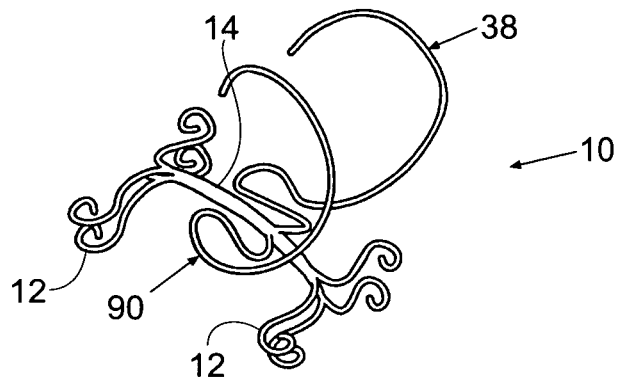
FIGS. 45 to 47 are side perspective views of a multi-functional elastic implants sized and configured to rest within or near the leaflet commissures of a dysfunctional heart valve annulus to reshape the annulus and restore leaflet coaptation as well serve as a leaflet retainer to prevent a native valve leaflet from being pushed into the atrium upon ventricular contraction, the implants also including a framework that serves to help position and secure the implant in situ.
Figure 46:
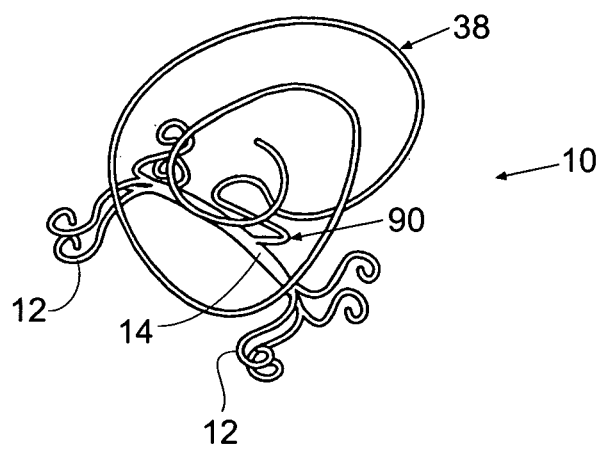
Figure 47:
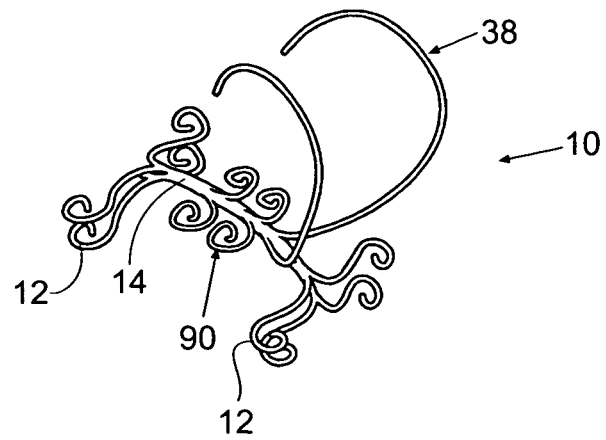

As further examples of multi-functional implants, FIGS. 45 to 47 shows an annulus remodeling implant 10 in which the rails further include a framework 38 (as previously described) to help position and secure the device in situ. In FIGS. 45 to 47, the framework 38 also includes as a leaflet retaining structure 90, as just described.

While the new devices and methods have been more specifically described in the context of the treatment of a mitral heart valve, it should be understood that other heart valve types can be treated in the same or equivalent fashion. By way of example, and not by limitation, the present systems and methods could be used in any heart valve annulus, including the tricuspid valve, the pulmonary valve, or the aortic valve. In addition, other embodiments and uses of the invention will be apparent to those skilled in the art from consideration of the specification and practice of the invention disclosed herein. The specification and examples should be considered exemplary and merely descriptive of key technical; features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

We claimed:

1. A method of treating a heart valve having a native heart valve annulus, valve leaflets and valve leaflet commissures positioned on opposite ends of a major axis of the heart valve annulus, the method comprising:
    introducing an implant into a chamber of the heart valve, the implant having one or more rails extending between a first strut and a second strut,
    and
    deploying the implant
    by engaging the valve leaflet commissures on opposite ends of the major axis of the heart valve annulus with the first and second struts so as to anchor the implant by a compressive loading of the one or more rails in a direction along the major axis so as to repair, replace or supplement the native heart valve with the implant,
    wherein the implant anchors by engaging internal cardiac tissues without penetrating or engaging an outer epicardial surface and the one or more rails extend in a direction along the major axis.

2. The method of claim 1
    wherein introducing the implant includes carrying the implant in a collapsed configuration within a sheath during intravascular deliver to the heart valve annulus, and withdrawing the sheath to deliver the implant at the heart valve annulus.

3. The method of claim 1 wherein introducing the implant further comprises advancing a catheter along an intravascular path, the catheter having a column strength to maintain force on the first strut during deployment.

4. The method of claim 1 wherein deploying the implant includes placing the first strut into contact with tissue at a first native valve leaflet commissure and subsequently placing the second strut into contact with tissue at a second native valve leaflet commissure while the one or more rails urges the first and second struts away from each other so as to elongate the major axis of the native heart valve after deployment.

5. The method of claim 1 further comprising:
outwardly displacing tissue along the major axis of the heart valve annulus thereby reshaping the native mitral heart valve annulus to improve coaptation of the native valve.

6. The method of claim 1 wherein the implant further comprises a pseudo-annulus that replaces valve function of the native valve annulus.

7. The method of claim 1 wherein the implant further comprises a neoleaflet element coupled to the one or more rails that supplements or replaces the native valve annulus when deployed.

8. The method of claim 1 wherein the one or more rails define a fabric covered bridge structure that supplements or replaces the native valve annulus when deployed.

9. The method of claim 1 wherein the implant is foldable between a delivery configuration and a deployed configuration such that deploying the implant comprises unfolding the implant.

10. The method of claim 9 wherein unfolding the implant comprises moving one or more tether or wire loops engaged with the implant.

11. The method of claim 1 wherein the rail is elastic such that the implant is movable to an elastically loaded state, wherein deploying the implant comprises:
prior to the elastic body being moved to the elastically loaded state of net compression, maintaining force on the first strut to elastically inwardly compress the elastic body while subsequently placing the second strut into contact with tissue at or near the second valve commissure to place the elastic rail under compressive load.

12. The method of claim 11, wherein the rail is defined in a shape so as to provide a spring constant when under a compressive load applied between the first and second struts thereby providing compliance to allow the implant to adapt to tissue morphology during use.

13. The method of claim 1, wherein the one or more rails circumscribe the native heart annulus within the chamber in which the heart valve is located.

14. The method of claim 13 wherein the native heart valve comprises a mitral valve or a tricuspid valve.

15. The method of claim 14, further comprising:
establishing an intravascular path that extends from a right atrium through a septum into the left atrium.

16. A method of treating a heart valve having a native heart valve annulus with valve leaflets and valve leaflet commissures on opposite ends of a major axis of the heart valve annulus, the method comprising:
introducing an implant into a chamber of the heart valve, the implant having one or more rails extending between opposing curvilinear engagement surfaces, the one or more rails sized and configured to extend between the opposing curvilinear engagement surfaces;
deploying the implant so as to engage the valve leaflet commissures on opposite ends of the major axis of the heart valve annulus with the opposing curvilinear engagement surfaces, respectively;
anchoring the implant within the native heart valve annulus by a compressive loading of the one or more rails while opposing curvilinear surfaces are engaged with the opposing valve leaflet commissures, wherein the implant anchors by engaging internal tissues without penetrating or engaging an outer epicardial surface and the one or more rails extending in a direction along the major axis; and
repairing, replacing or supplementing the native heart valve annulus with the implant.

17. The method of claim 16, wherein the one or more rails are defined within a bridge structure that extends about the native heart annulus within the chamber in which the heart valve is located.

18. The method of claim 16, wherein anchoring comprising engaging the valve leaflet commissures with the opposing curvilinear engagement surfaces such that each curvilinear surface engages tissue within the atrium above the commissure and engages tissue within a ventricle below the commissure.

19. The method of claim 16, wherein the implant is foldable between a collapsed configuration for intravascular delivery and an expanded configuration for deployment such that deploying the implant comprises unfolding the implant by moving one or more tethers or wire loops engaged with the implant.

20. The method of claim 16, wherein the implant comprises a fabric covered bridge structure supported by the one or more rails, the fabric covered bridge structure including one or more neo-leaflets that supplement or replace function of the native valve annulus when deployed.

21. A method of treating a heart valve having a native heart valve annulus, the annulus having a major axis and a minor axis, valve leaflets and valve leaflet commissures positioned on opposite ends of a major axis, the method comprising:
introducing an implant into a chamber of the heart valve, the implant having one or more rails extending between a first strut and a second strut, the one or more rails having a spring constant that, when the one or more rails are compressed, urges the first strut and the second strut away from each other; and
deploying the implant by engaging the implant with the annulus with the one or more rails above the native heart valve and the first and second struts engaging tissue at the lengthwise ends of the major axis in a compressed condition such that the first and second struts are urged away from each other to stretch the annulus lengthwise along its major axis while allowing the sides of the annulus to approach each other along the minor axis.

* * * * *